(12) United States Patent
Rooney et al.

(10) Patent No.: US 10,772,914 B1
(45) Date of Patent: Sep. 15, 2020

(54) EBV-SPECIFIC IMMUNE CELLS

(71) Applicant: Baylor College of Medicine, Houston, TX (US)

(72) Inventors: Cliona M. Rooney, Bellaire, TX (US); Sandhya Sharma, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 16/388,776

(22) Filed: Apr. 18, 2019

(51) Int. Cl.
*A61K 35/17* (2015.01)
*C12N 5/0783* (2010.01)
*A61P 35/00* (2006.01)
*C07K 14/05* (2006.01)

(52) U.S. Cl.
CPC .............. *A61K 35/17* (2013.01); *A61P 35/00* (2018.01); *C07K 14/05* (2013.01); *C12N 5/0638* (2013.01)

(58) Field of Classification Search
CPC ..................................................... A61K 35/17
See application file for complete search history.

(56) References Cited

U.S. PATENT DOCUMENTS

| | | | |
|---|---|---|---|
| 5,641,628 | A | 6/1997 | Bianchi |
| 6,274,378 | B1 | 8/2001 | Steinman et al. |
| 6,455,299 | B1 | 9/2002 | Steinman et al. |
| 6,821,778 | B1 | 11/2004 | Engleman et al. |
| 7,785,875 | B2 | 8/2010 | Hwang et al. |
| 8,481,051 | B2 | 7/2013 | Kuzushima et al. |
| 9,255,243 | B2 | 2/2016 | Wilson et al. |
| 9,963,677 | B2 | 5/2018 | Leen et al. |
| 2004/0022761 | A1 | 2/2004 | Banchereau et al. |
| 2005/0028505 | A1 | 2/2005 | Schumacher |
| 2005/0106717 | A1 | 5/2005 | Wilson et al. |
| 2006/0045883 | A1 | 3/2006 | Molldrem et al. |
| 2006/0073126 | A1 | 4/2006 | Shiku et al. |
| 2008/0260701 | A1 | 10/2008 | Hope |
| 2009/0305324 | A1 | 12/2009 | Kuzushima et al. |
| 2011/0182870 | A1* | 7/2011 | Leen ...................... A61K 39/12 424/93.71 |
| 2015/0010519 | A1 | 1/2015 | Leen et al. |
| 2015/0044258 | A1 | 2/2015 | Knaus et al. |
| 2016/0208216 | A1* | 7/2016 | Vera ........................ A61K 35/17 |
| 2016/0362658 | A1 | 12/2016 | Leen et al. |

FOREIGN PATENT DOCUMENTS

| | | |
|---|---|---|
| WO | 2005028505 A2 | 3/2005 |
| WO | 2005035728 A2 | 4/2005 |
| WO | 2007121276 A2 | 10/2007 |
| WO | 2008073313 A2 | 6/2008 |
| WO | 2009053109 A1 | 4/2009 |
| WO | 2011/028531 A1 | 3/2011 |
| WO | 2013088147 A1 | 6/2013 |
| WO | 2016/073595 A8 | 6/2016 |

OTHER PUBLICATIONS

Calarota et al. (Immunology. 2013: 139: 533-544). (Year: 2013).*
Bensussan et al. "Detection of membrane-bound HLA-G translated products with a specific monoclonal antibody", Proc. Natl. Acad. Sci. USA, 92:10292-10296, 1995.
Binggeli et al., American Journal of Transplantation, 2007, vol. 7, pp. 1131-1139.
Blyth et al., "Bk Vims Specific T Cells Expanded Ex Vivo for Use in Cellular Therapy Show Multiple Antigen Specificity and Polyfunctional THI Responses", abstract #164, S215.
Blyth et al "BK Vims-Specific T Cells for Use in Cellular Therapy Show Specificity to Multiple Antigens and Polyfunctional Cytokine Responses", Transplantation, 92(10):1077-1084, 2011.
Blyth et al., in Blood, (Nov. 20, 2009) vol. 114, No. 22, pp. 962, Meeting Info.: 51st Annual Meeting of the American-Society-of-Hematology, New Orleans, LA, USA. Dec. 5-8, 2009, Amer Soc Hematol.
Can and Karahuseyinoglu, "Concise review: human umbilical cord stroma with regard to the source of fetus-derived stem cells", Stem Cells, 25:2886-2895, 2007.
Chakera et al., Clin Exp. Immuno12011, Sep. 156 (3): 401-409.
Dasari et al., "Prophylactic and therapeutic adenoviral vector-based multivims-specific Tcell immunotherapy for transplant patients", Mal. Ther., 3: 16058, 2016.
Dunne et al., "Selective Expansion and Partial Activation of Human NK Cells and NK Receptor-Positive T Cells by IL-2 and IL-15", Journal of Immunology, 2001, pp. 3129-3138.
Gaundar et al., "The Generation of Clinical Grade Aspergillus Fumigatus (AF) Specific Immune Cells for Adoptive Immunotherapy", abstract #168, S216.
Vera, Juan F., et al; "Accelerated Production of Antigen-Specific T-cells for Pre-Clinical and Clinical Applications using Gas-Permeable Rapid Expansion Cultureware (G-Rex)"; Journal of Immunotherapy, Apr. 2010, vol. 33, No. 3, pp. 305-315.
Gerdemann et al., "Cytotoxic T lymphocytes simultaneously targeting multiple tumor-associates antigens to treat EBV negative lymphoma", Molecular Therapy, Nature Publishing Group, GB, vol. 19, No. 12, Dec. 1, 2011, pp. 2258-2268.
Gerdemann et al., "Generation of Multivirus-specific T Cellls to Prevent/treat Viral Infections aftr Allogeneic Hematopoietic Stem Cell Transplant", Journal of Visualized Experiments, May 2011, vol. 51, e2736, pp. 1-6.
Gerdemann et al., "Multivirus-specific CTL for Adoptive Transfer Using In Vitro Pepmix Stimulation", Biology Blood Marrow Transplant, online Jan. 28, 2011, p. S216.

(Continued)

*Primary Examiner* — Scott Long

(57) ABSTRACT

Methods for generating/expanding populations of immune cells comprising immune cells specific for an Epstein Barr Virus (EBV) lytic antigen are disclosed, the methods comprising stimulating immune cells specific for an EBV lytic antigen by contacting peripheral blood mononuclear cells (PBMCs) with: (i) one or more peptides corresponding to all or part of one or more EBV lytic antigens; or (ii) antigen presenting cells (APCs) presenting one or more peptides corresponding to all or part of one or more EBV lytic antigens. Also disclosed are populations of immune cells comprising immune cells specific for an EBV lytic antigen expanded according to such methods, and uses thereof.

13 Claims, 15 Drawing Sheets

(56) References Cited

OTHER PUBLICATIONS

Gerdemann et al., "Nucleofection of DCs to Generate Multivirus-specific T Cells for Prevention or Treatment of Viral Infections in the Immunocompromised Host", Molecular Therapy, vol. 17, No. 9, 1 Sep. 2009, pp. 1616-1625.
Y E Z, et al; In Vitro expansion and Charcterization of Dendritic Cells Derived from Human Bon Marroe CD34+ Cells; Bone Marrow Transpaln, 1996, v 18. 997-1008.
Gerdemann et al., "Rapidly Generated Multivirus-specific Cytotoxic T Lymphocytes for the Prophylaxis and Treatment of Viral Infections", Molecular Therapy 2012, vol. 20, No. 8, pp. 1622-1632.
Gerdemann et al., "Safety and clinical efficacy of rapidly-generated trivirus-directed T cells as treatment for adenovirus, EBV, and CMV infections after allogeneic hematopoietic stem cell transplant", Molecular Therapy, vol. 2, No. 11, Jun. 20, 2013, pp. 2112-2121.
Hobeika et al., "Detailed analysis of cytomegalovirus (CMV)-specific T cells expanded for adoptive immunotherapy of CMV infection following allogeneic stem cell transplantation for malignant disease", Intl. Society for cellular Therapy, Cytotherapy, 2008, vol. 10, No. 3, pp. 289-302.
International Preliminary Report on Patentablility dated Feb. 10, 2014, during prosecution of International Application No. PCT/GB2012/053113.
International Search Report and Written Opinion issued in International Application No. PCT/US2010/46505, dated Oct. 14, 2010.
Jennes et al., "Enhanced ELISPOT detection of antigen-specific T cell responses from cryopreserved specimens with addition of both IL-7 and IL-15 the Amplispot assay" Journal of Immunological Methods, 2002, vol. 270, pp. 99-108.
Kedl et al; "T Cells Compete for Antigen-bearing Antigen-presenting Cells"; J.P. Med.—The Rockfeller University Press—vol. 192, No. 8, Oct. 16, 2002.
Kedl et al; "T Cells Down-Modulate Peptide-MHC Complexes on APCs in vivo"; Published online: Dec. 3, 2001, DOI: 10.1 038/ni/742; 2002 Nature Publishing Group.
Khanna et al., Blood, Jul. 2011, vol. 118, No. 4, pp. 1121-1131.
Lapteva and Vera " Optimization Manufacture of Virus- and Tumor-Specific T Cells", Stem Cells International, Apr. 26, 2011, vol. 2011, pp. 1-8.
Leen et al., "Cytotoxic lymphocyte (CTL) therapy for the treatment of EBV negative tumors", Abstract, International Society for Cell and Gene Therapy of Cancer Annual Meeting held in Cork, Ireland, presented Sep. 4, 2009.
Leen et al., "Identification of hexon-specific CD4 and CDS T-cell epitopes for vaccine and immunotherapy," Journal of Virology, 82(1):546-554, 2008.
Leen et al., "Overcoming antigenic competition to produce multispecific cytotoxic T lymphocyte lines for adoptive transfer," Poster, 6th Annual Dan L. Duncan Cancer Center Symposium, Baylor College of Medicine, Feb. 2009, No. 374, p. 134.
Leen et al., Nature Medicine, 2006, vol. 12, No. 10, pp. 1160-1166.
Liao et al., "Transfection of RNA encoding tumor antigens following maturation of dendritic cells leads to prolonged presentation of antigen and the generation of high-affinity tumor-reactive cytotoxic T lymphocytes", Molecular Therapy, May 1, 2004, vol. 9, No. 5, pp. 757-764.
Lim et al. Journal of Translational Medicine 2009, vol. 7:72, pp. 1-11.
Maecker et al., Journal of Immunological Methods, 2001, vol. 55, pp. 27-40.
Montes et al., "Optimum in vitro expansion of human antigen-specific CD8+ T cells for adoptive transfer therapy", British Society for Immunology, Clinical and Experimental Immunology, 2005, vol. 142, pp. 292-302.
Morandi et al., "TUMOR mRNA-Transfected Dendritic Cells Stimulate the Generation of CTL that Recognize Neuroblastoma-Associated Antigens, Kill Tumor Cells: Immunotherapeutic Implications", Neoplasia, Oct. 1, 2006, vol. 8, No. 10, pp. 833-842.
Muftuoglu et al., "Use of Expanded Allogeneic Third Party BK Vims Specific Cytotoxic C6. T Cells to Target Progressive Multifocal Leukoencephalopathy",Am. Soc. Hematol., abstract #98495, 128(22):3365, 2016.
Na et al., "Human Bone Marrow as a Source of Multifunctional CMV-Specific CD4+ T Cells for Adoptive Cell Therapy" BLOOD, 2007, vol. 110, p. 2973.
Nair et al, "Induction of tumor-specific cyototoxic T lymphocytes in cancer patients by autologous tumor RNA-transfected dendritic cells", Annals of Surgery, Apr. 1, 2002, vol. 235, No. 4, pp. 540-549.
Olson et al., "Efficacy of Third Party Bk Vims (BKV) Specific Cytotoxic T-Lymphocytes Generated by Ex Vivo Expansion for the Treatment of BKV Infection in Stem Cell Transplant Recipients, a Phase 2 Trial", Am. Soc. Hematol., abstract, 128(22):504, 2016.
Ramaswami et al., Clin Vaccine Immunol, Published on line Mar. 2, 2011, vol. 18, No. 5 815-824.
Suneetha et al., Journal of Immunological Methods, 2009, vol. 342, No. 1-2, pp. 33-48.
Testa et al: "MHC Class I-Presented T Cell Epitopes Identified by Immunoproteomics Analysis Are Targets for a Cross Reactive Influenza-Specific T Cell Response", PLOS ONE, vol. 7, No. 11, Nov. 7, 2012 (Nov. 7, 2012), p. e48484.
Trivedi et al., "Generation of CMV-specific T lymphocytes using protein-spanning pools of pp65-derived overlapping pentadecapeptides for adoptive immunotherapy", BLOOD, Apr. 1, 2005, vol. 105, No. 7, pp. 2793-2794.
van Montfoort et al., "Antigen storage compartments in mature dendritic cells facilitate prolonged cytotoxic T lymphocyte cross-priming capacity", PNAS, Apr. 21, 2009, vol. 106, No. 16, pp. 6730-6735.
Vella et al., "Cytokine-induced survival of activated T cells in vitro and in vivo", Proc. Natl. Acad. Sci. USA 95, Immunology, Mar. 1998, vol. 95, pp. 3810-3815.
Tekkatte, Chandana, et al; ""Humanized" Stem Cell Culture Techniques: The Animal Serum Controversy"; Stem Cells Int'l, vol. 2011; Article ID 504723; 14 pgs; Nov. 9, 2010.
Chia, Whay-Kuang, et al; "Adoptive T-Cell Transfer and Chemotherapy in the First-Line Treatment of Metastatic and/or Locally Recurrent Nasopharyngeal Carcinoma"; The Am. Society of Gene & Cell Therapy,; Molecular Therapy; pp. 1-8; Jul. 29, 2013.
Jeffes III et al. "Therapy of recurrent high grade gliomas with surgery, and autologous mitogen activated IL-2 stimulated killer (MAK) Lymphocytes: I. Enchancement of MAK lytic activity and cytokine production by PHA and clinical use of PHA" Journal of Neuro-Oncology, 1993, vol. 15, pp. 141-155.
Geyeregger et al. "Short-Term In-Vitro Expansion Improves Monitoring and Allows Affordable Generation of Virus-Specific T-Cells against Several Viruses for a Broad Clinical Application" PLoS ONE, 2013, 8(4): e59592.

* cited by examiner

EBV-SPECIFIC IMMUNE CELLS

STATEMENT REGARDING FEDERALLY SPONSORED RESEARCH OR DEVELOPMENT

This invention was made with government support under Grant Number NIH-NCI P50 CA126752 awarded by the National Institute of Health. The government has certain rights in the invention.

TECHNICAL FIELD

The present disclosure relates to molecular and cell biology, and also relates to methods of medical treatment and prophylaxis.

BACKGROUND

Around 40% of lymphomas, all undifferentiated nasopharyngeal carcinomas (NPC) and about 10% of gastric cancers carry the Epstein-Barr virus (EBV) genome and express viral proteins that can be targeted by adoptively transferred EBV-specific T cells (EBVSTs).

EBV+ malignancies occurring outside the setting of immunosuppression express only 1 to 4 of about 90 EBV proteins and whilst these antigens are poorly immunogenic, they provide target antigens for EBVSTs.

Ongoing clinical trials concerning the use of EBV-specific T cells to treat EBV-positive malignancies employ EBV-transformed B cells in the expansion of EBV-specific T cells (NCT02578641), or involve stimulating PBMCs with peptides corresponding to EBV type II latency antigens (NCT01555892).

BRIEF SUMMARY

The present disclosure is based on the unexpected finding that peptides corresponding to EBV lytic antigens can be used to generate/expand populations of EBV-specific immune cells which are useful for the treatment of EBV-associated diseases.

Despite the fact that cells infected with EBV in EBV-associated diseases only display substantial expression of EBV latent antigens, the inventors demonstrate herein that populations of immune cells generated/expanded by stimulating immune cells using peptides of EBV lytic antigens display cytolytic activity against EBV-infected cells. Moreover, populations of immune cells generated/expanded by stimulating immune cells using peptides of EBV lytic antigens are demonstrated to display similar or improved ability to treat EBV-positive cancer in vivo as compared to populations of immune cells generated/expanded by stimulating immune cells using peptides of EBV latent antigens.

Another unexpected finding was that methods using both EBV lytic antigens and EBV latent antigens in stimulations did not result in a substantial reduction of the frequency of immune cells specific for EBV latent antigens in the expanded population.

The inventors further demonstrate that populations of immune cells comprising immune cells specific for EBV lytic antigens and immune cells specific for EBV latent antigens are more effective for treating EBV-associated disease than populations of immune cells comprising immune cells specific for EBV latent antigens only.

In a first aspect the present disclosure provides a method for generating or expanding a population of immune cells comprising immune cells specific for an Epstein Barr Virus (EBV) lytic antigen, comprising stimulating immune cells specific for an EBV lytic antigen by contacting peripheral blood mononuclear cells (PBMCs) with: (i) one or more peptides corresponding to all or part of one or more EBV lytic antigens; or (ii) antigen presenting cells (APCs) presenting one or more peptides corresponding to all or part of one or more EBV lytic antigens.

In some embodiments the method further comprises re-stimulating the immune cells specific for an EBV lytic antigen by contacting them with APCs presenting one or more peptides corresponding to all or part of one or more EBV lytic antigens.

Also provided is a method for generating or expanding a population of immune cells comprising immune cells specific for an Epstein Barr Virus (EBV) lytic antigen and immune cells specific for an EBV latent antigen, comprising stimulating immune cells specific for an EBV lytic antigen and immune cells specific for an EBV latent antigen by contacting peripheral blood mononuclear cells (PBMCs) with: (i) one or more peptides corresponding to all or part of one or more EBV lytic antigens, and one or more peptides corresponding to all or part of one or more EBV latent antigens; or (ii) antigen presenting cells (APCs) presenting one or more peptides corresponding to all or part of one or more EBV lytic antigens, and one or more peptides corresponding to all or part of an EBV latent antigen.

In some embodiments the method further comprises re-stimulating the immune cells specific for an EBV lytic antigen and the immune cells specific for an EBV latent antigen by contacting them with APCs presenting one or more peptides corresponding to all or part of one or more EBV lytic antigens, and one or more peptides corresponding to all or part of an EBV latent antigen.

In some embodiments in accordance with various aspects of the present disclosure the one or more EBV lytic antigens are selected from BZLF1, BRLF1, BMLF1, BMRF1, BXLF1, BALF1, BALF2, BGLF5, BHRF1, BNLF2A, BNLF2B, BHLF1, BLLF2, BKRF4, BMRF2, BALF4, BILF1, BILF2, BNFR1, BVRF2, BALF3, BALF5 and BDLF3.

In some embodiments the one or more EBV lytic antigens are selected from BZLF1, BRLF1, BMLF1, BMRF1, BALF2, BNLF2A, BNLF2B, BMRF2 and BDLF3.

In some embodiments the one or more EBV latent antigens are selected from EBNA1, EBNA-LP, EBNA2, EBNA3A, EBNA3B, EBNA3C, BARF1, LMP1, LMP2A and LMP2B.

In some embodiments the one or more EBV latent antigens are selected from EBNA1, LMP1, LMP2A and LMP2B.

In some embodiments the PBMCs are PBMCs depleted of CD45RA-positive cells.

Also provided is an isolated population of immune cells obtained or obtainable by a method according to the present disclosure.

Also provided is an isolated population of immune cells comprising immune cells specific for an Epstein Barr Virus (EBV) lytic antigen.

Also provided is an isolated population of immune cells comprising immune cells specific for an Epstein Barr Virus (EBV) lytic antigen and immune cells specific for an EBV latent antigen.

Also provided is a pharmaceutical composition comprising an isolated population of immune cells according to the present disclosure.

Also provided is an isolated population of immune cells or a pharmaceutical composition according to the present disclosure, for use in a method of treatment or prevention of a disease or disorder associated with EBV infection.

Also provided is the use of isolated population of immune cells or a pharmaceutical composition according to the present disclosure, in the manufacture of a medicament for use in a method of treatment or prevention of a disease or disorder associated with EBV infection.

Also provided is a method for treating or preventing a disease or disorder associated with EBV infection, comprising administering an isolated population of immune cells or a pharmaceutical composition according to the present disclosure, to a subject.

Also provided is an isolated population of immune cells or a pharmaceutical composition according to the present disclosure, for use in a method of treatment or prevention of a cancer.

Also provided is the use of an isolated population of immune cells or a pharmaceutical composition according to the present disclosure, in the manufacture of a medicament for use in a method of treatment or prevention of a cancer.

Also provided is a method for treating or preventing a cancer, comprising administering an isolated population of immune cells or a pharmaceutical composition according to the present disclosure, to a subject.

In some embodiments in accordance with the various aspects of the present disclosure the cancer is an EBV-associated cancer.

In some embodiments the EBV-associated cancer is selected from EBV-positive lymphoma, EBV-positive nasopharyngeal carcinoma, and EBV-positive gastric carcinoma.

Also provided is a method for killing a cell infected with EBV, comprising contacting a cell infected with EBV with an isolated population of immune cells or a pharmaceutical composition according to the present disclosure. The method may be an in vitro or an in vivo method.

Also provided is the use of an isolated population of immune cells or a pharmaceutical composition according to the present disclosure to kill a cell infected with EBV.

DESCRIPTION

The present disclosure is based on the unexpected finding that immune cells specific for EBV lytic antigens are capable of killing EBV-infected cells, and that populations of cells comprising immune cells specific for EBV latent antigens and EBV lytic antigens display improved ability to control EBV-positive malignancies as compared to populations of cells only comprising immune cells specific for EBV latent antigens.

Epstein-Barr Virus replication Epstein-Barr Virus (EBV) virology is described e.g. in Stanfield and Luftiq, F1000Res. (2017) 6:386 and Odumade et al., Clin Microbiol Rev (2011) 24(1):193-209, both of which are hereby incorporated by reference in entirety.

EBV infects epithelial cells via binding of viral protein BMRF2 to β1 integrins, and binding of viral protein gH/gL with integrins avβ6 and avβ8. EBV infects B cells through interaction of viral glycoprotein gp350 with CD21 and/or CD35, followed by interaction of viral gp42 with MHC class II. These interactions trigger fusion of the viral envelope with the cell membrane, allowing the virus to enter the cell. Once inside, the viral capsid dissolves and the viral genome is transported to the nucleus.

EBV has two modes of replication; latent and lytic.

The latent cycle does not result in production of virions, and can take place in place B cells and epithelial cells. The EBV genome circular DNA resides in the cell nucleus as an episome and is copied by the host cell's DNA polymerase. In latency, only a fraction of EBV's genes are expressed, in one of three different patterns known as latency programs, which produce distinct sets of viral proteins and RNAs. The latent cycle is described e.g. in Amon and Farrell, Reviews in Medical Virology (2004) 15(3): 149-56, which is hereby incorporated by reference in entirety.

EBNA1 protein and non-coding RNA EBER are expressed in each of latency programs I-Ill. Latency programs II and III further involve expression of EBNALP, LMP1, LMP2A and LMP2B proteins, and latency program III further involves expression of EBNA2, EBNA3A, EBNA3B and EBNA3C.

EBNA1 is multifunctional, and has roles in gene regulation, extrachromosomal replication, and maintenance of the EBV episomal genome through positive and negative regulation of viral promoters (Duellman et al., J Gen Virol. (2009); 90(Pt 9): 2251-2259). EBNA2 is involved in the regulation of latent viral transcription and contributes to the immortalization of cells infected with EBV (Kempkes and Ling, Curr Top Microbiol Immunol. (2015) 391:35-59). EBNA-LP is required for transformation of native B cells, and recruits transcription factors for viral replication (Szymula et al., PLoS Pathog. (2018); 14(2):e1006890). EBNA3A, 3B and 3C interact with RBPJ to influence gene expression, contributing to survival and growth of infected cells (Wang et al., J Virol. (2016) 90(6):2906-2919). LMP1 regulates expression of genes involved in B cell activation (Chang et al., J. Biomed. Sci. (2003) 10(5): 490-504). LMP2A and LMP2B inhibit normal B-cell signal transduction by mimicking the activated B-cell receptor (Portis and Longnecker, Oncogene (2004) 23(53): 8619-8628). EBERs form ribonucleoprotein complexes with host cell proteins, and are proposed to have roles in cell transformation.

The latent cycle can progress according to any of latency programs I to III in B cells, and usually progresses from III to II to I. Upon infection of a resting naïve B cell, EBV enters latency program III. Expression of latency III genes activates the B cell, which becomes a proliferating blast. EBV then typically progresses to latency II by restricting expression to a subset of genes, which cause differentiation of the blast to a memory B cell. Further restriction of gene expression causes EBV to enter latency I. EBNA1 expression allows EBV to replicate when the memory B cell divides. In epithelial cells, only latency II occurs.

In primary infection, EBV replicates in oropharyngeal epithelial cells and establishes Latency III, II, and I infections in B-lymphocytes. EBV latent infection of B-lymphocytes is necessary for virus persistence, subsequent replication in epithelial cells, and release of infectious virus into saliva. EBV Latency III and II infections of B-lymphocytes, Latency II infection of oral epithelial cells, and Latency II infection of NK- or T-cell can result in malignancies, marked by uniform EBV genome presence and gene expression.[26]

Latent EBV in B cells can be reactivated to switch to lytic replication. The lytic cycle results in the production of infectious virions and can take place in place B cells and epithelial cells, and is reviewed e.g. by Kenney in Chapter 25 of Arvin et al., Human Herpesviruses: Biology, Therapy and Immunoprophylaxis; Cambridge University Press (2007), which is hereby incorporated by reference in entirety.

Lytic replication requires the EBV genome to be linear. The latent EBV genome is episomal, and so it must be linearised for lytic reactivation. In B cells, lytic replication normally only takes place after reactivation from latency.

Immediate-early lytic gene products such as BZLF1 and BRLF1 act as transactivators, enhancing their own expression, and the expression of later lytic cycle genes.

Early lytic gene products have roles in viral replication (e.g. EBV DNA polymerase catalytic component BALF5; DNA polymerase processivity factor BMRF1, DNA binding protein BALF2, helicase BBLF4, primase BSLF1, and primase-associated protein BBLF2/3) and deoxynucleotide metabolism (e.g. thymidine kinase BXLF1, dUTPase BORF2). Other early lytic gene products act transcription factors (e.g. BMRF1, BRRF1), have roles in RNA stability and processing (e.g. BMLF1), or are involved in immune evasion (e.g. BHRF1, which inhibits apoptosis).

Late lytic gene products are traditionally classed as those expressed after the onset of viral replication. They generally encode structural components of the virion such as nucleocapsid proteins, as well as glycoproteins which mediate EBV binding and fusion (e.g. gp350/220, gp85, gp42, gp25). Other late lytic gene products have roles in immune evasion; BCLF1 encodes a viral homologue of IL-10, and BALF1 encodes a protein with homology to the anti-apoptotic protein Bcl2.

EBV Antigen Expression in EBV-Associated Cancers

EBV antigens expressed in EBV-positive cancers are described e.g. in Craddock and Heslop Update Cancer Ther. (2008) March; 3(1): 33-41, Gottschalk and Rooney Curr Top Microbiol Immunol. (2015) 391: 427-454, and Shinozaki-Ushiku et al., Int J Oncol. (2015) 46(4):1421-34.

EBV-associated lymphoma arising in immunocompromised subjects e.g. following HSCT or solid organ transplant, subjects having congenital immunodeficiency or HIV infection display type III latency, and express EBNA1, EBNA2, EBNA-LP, EBNA3A, EBNA3B, EBNA3C, BARF1, LMP1 and LMP2. EBV-associated EBV-positive Hodgkin's lymphoma, non-Hodgkin's lymphoma, some types and T cell lymphoma, NK cell lymphoma, some cases of B-cell lymphoma and nasopharyngeal carcinoma display type II latency, and express EBNA1, BARF1, LMP1 and LMP2. EBV-positive Burkitt's lymphoma displays type I latency, expressing EBNA1 and BARF1. EBV-positive gastric carcinoma displays type I or type II latency.

It has previously been thought that only EBV latent antigens (and not lytic cycle antigens) are expressed by cells of EBV-positive cancer cells in immunocompetent subjects. Transcripts encoding lytic cycle gene products have recently been detected in EBV-positive malignancies including gastric carcinoma, nasopharyngeal carcinoma and B cell lymphoma.

It has not yet been determined whether it is possible to generate populations of immune cells specific for EBV lytic antigens from patients having EBV-positive cancers or healthy donor subjects, whether immune cells specific for EBV lytic antigens would display effector activity against EBV-infected cells, or whether populations of immune cells specific for EBV lytic antigens would be useful to treat EBV-associated cancers.

EBV Antigens

Aspects of the present disclosure employ peptides corresponding to EBV antigens.

In some embodiments in accordance with the various aspects of the present disclosure, an EBV lytic antigen is selected from BZLF1, BRLF1, BMLF1, BMRF1, BXLF1, BALF1, BALF2, BARF1, BGLF5, BHRF1, BNLF2A, BNLF2B, BHLF1, BLLF2, BKRF4, BMRF2, FU, EBNA1-FUK, BALF4, BILF1, BILF2, BNFR1, BVRF2, BALF3, BALF5, BDLF3 and gp350. In some embodiments, an EBV lytic antigen is selected from BZLF1, BRLF1, BMLF1, BMRF1, BXLF1, BALF1, BALF2, BGLF5, BHRF1, BNLF2A, BNLF2B, BHLF1, BLLF2, BKRF4, BMRF2, BALF4, BILF1, BILF2, BNFR1, BVRF2, BALF3, BALF5 and BDLF3. In some embodiments, an EBV lytic antigen is selected from BZLF1, BRLF1, BMLF1, BMRF1, BALF2, BNLF2A, BNLF2B, BMRF2 and BDLF3.

In some embodiments, an EBV lytic antigen is selected from BZLF1, BRLF1, BMRF1, BMLF1, BXLF1, BALF1, BLLF2, BALF2, BNLF2A, BNLF2B and BMRF2. In some embodiments, an EBV lytic antigen is selected from BZLF1, BRLF1, BMRF1, BMLF1, BXLF1, BALF1, BLLF2, BALF2 and BNLF2A. In some embodiments, an EBV lytic antigen is selected from BZLF1, BRLF1, BMRF1, BMLF1, BALF2, BNLF2A, BNLF2B and BMRF2.

In some embodiments, an EBV lytic antigen is selected from an immediate-early lytic antigen, an early lytic antigen or a late lytic antigen.

In some embodiments an immediate-early lytic antigen is selected from BZLF1, BRLF1 and BMRF1.

In some embodiments an early lytic antigen is selected from BMLF1, BMRF1, BXLF1, BALF1, BALF2, BARF1, BGLF5, BHRF1, BNLF2A, BNLF2B, BHLF1, BLLF2, BKRF4, BMRF2, FU and EBNA1-FUK. In some embodiments an early lytic antigen is selected from BMLF1, BMRF1, BXLF1, BALF1, BALF2, BGLF5, BHRF1, BNLF2A, BNLF2B, BHLF1, BLLF2, BKRF4 and BMRF2. In some embodiments an early lytic antigen is selected from BMLF1, BMRF1, BALF2, BNLF2A, BNLF2B and BMRF2.

In some embodiments a late lytic antigen is selected from BALF4, BILF1, BILF2, BNFR1, BVRF2, BALF3, BALF5, BDLF3 and gp350. In some embodiments a late lytic antigen is selected from BALF4, BILF1, BILF2, BNFR1, BVRF2, BALF3, BALF5 and BDLF3. In some embodiments a late lytic antigen is BDLF3.

In some embodiments in accordance with the various aspects of the present disclosure, an EBV latent antigen is selected from EBNA1, EBNA-LP, EBNA2, EBNA3A, EBNA3B, EBNA3C, BARF1, LMP1, LMP2A and LMP2B. In some embodiments, an EBV latent antigen is selected from EBNA1, LMP1, LMP2A and LMP2B. In some embodiments, an EBV latent antigen is selected from EBNA1, LMP1 and LMP2A.

In some embodiments, an EBV latent antigen is selected from type III latency antigen, a type II latency antigen or a type I latency antigen.

In some embodiments a type III latency antigen is selected from EBNA1, EBNA-LP, LMP1, LMP2A, LMP2B, BARF1, EBNA2, EBNA3A, EBNA3B and EBNA3C. In some embodiments a type II latency antigen is selected from EBNA1, EBNA-LP, LMP1, LMP2A, LMP2B and BARF1. In some embodiments a type I latency antigen is selected from EBNA1 and BARF1.

Where an EBV antigen is referred to herein, the present disclosure also contemplates isoforms, fragments, variants (including mutants) of the given EBV antigen. The amino acid sequence for a given EBV antigen, e.g. an EBV antigen referred to herein, can be retrieved e.g. from The UniProt Knowledgebase (UniProtKB)—see The UniProt Consortium, Nucleic Acids Research (2019), 47(D1): D506-D515.

An "isoform", "fragment" or "variant" of a reference EBV antigen may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference EBV antigen (e.g. a reference isoform of the antigen).

A "fragment" generally refers to a fraction of the reference protein, and may be of any length (by number of amino acids), although may optionally be at least 20% of the length of the reference protein (that is, the protein from which the fragment is derived) and may have a maximum length of one of 50%, 75%, 80%, 85%, 90%, 95% or 99% of the length of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by EBV.

In some embodiments in accordance with the various aspects described herein, reference is made to "one or more" antigens from a given list. Reference to "one or more" antigens means anywhere between one and all of the antigens recited in the list. Depending on the number of antigens listed, reference to "one or more" can mean e.g. 1, 2, 3, 4, 5, 6, 7, 8, 9, 10, etc. of the recited antigens.

Peptides and Pepmixes

Aspects of the present disclosure employ peptides corresponding to EBV antigens in methods to generate/expand populations of immune cells specific for EBV antigens.

As used herein, a "peptide" refers to a chain of two or more amino acid monomers linked by peptide bonds. A peptide typically has a length in the region of about 2 to 50 amino acids. A "polypeptide" is a polymer chain of two or more peptides. Polypeptides typically have a length greater than about 50 amino acids.

As used herein, a peptide which "corresponds to" a reference antigen comprises or consists of an amino acid sequence of the reference antigen. For example, a peptide "corresponding to" EBNA1 comprises or consists of a sequence of amino acids which is found within the amino acid sequence of EBNA1 (i.e. is a subsequence of the amino acid sequence of EBNA1).

Peptides employed herein typically have a length of 5-30 amino acids, e.g. one of 5-25 amino acids, 10-20 amino acids, or 12-18 amino acids. In some embodiments, peptides have a length of one of 5, 6, 7, 8, 9, 10, 11, 12, 13, 14, 15, 16, 17, 18, 19 or 20 amino acids. In some embodiments, peptides have a length of about 15 amino acids.

"Peptides" as used herein may refer to populations comprising non-identical peptides.

In some embodiments in accordance with various aspects of the present disclosure, the methods employ peptides corresponding to more than one antigen. In such embodiments, there is at least one peptide which corresponds to each of the antigens. For example, where the methods employ peptides corresponding to EBNA1 and LMP1, the peptides comprise at least one peptide corresponding to EBNA1, and at least one peptide corresponding to LMP1.

In some embodiments the methods employ peptides corresponding to all or part of a reference antigen. Peptides corresponding to all of a given antigen cover the full length of the amino acid sequence of the antigen. That is to say that together, the peptides contain all of the amino acids of the amino acid sequence of the given antigen.

Peptides corresponding to part of a given antigen cover part of the amino acid sequence of the antigen. In some embodiments where peptides cover part of the amino acid sequence of the antigen, the peptides together may cover e.g. greater than 10%, e.g. greater than one of 15%, 20%, 25%, 30%, 35%, 40%, 45%, 50%, 55%, 60%, 65%, 70%, 75%, 80%, 85%, 90% or 95% of the amino acid sequence of the antigen.

In some embodiments the methods employ overlapping peptides. "Overlapping" have amino acids, and more typically sequences of amino acids, in common. By way of illustration, a first peptide consists of an amino acid sequence corresponding to positions 1 to 15 of the amino acid sequence of EBNA1, and a second peptide consists of an amino acid sequence corresponding to positions 5 to 20 of the amino acid sequence of EBNA1. The first and second peptides are overlapping peptides corresponding to EBNA1, overlapping by 11 amino acids.

In some embodiments overlapping peptides overlap by one of 1-20, 5-20, 8-15 or 10-12 amino acids. In some embodiments overlapping peptides overlap by one of 1, 2, 3, 4, 5, 6, 7, 8, 9, 10, 11, 12, 13, 14 or 15 amino acids. In some embodiments overlapping peptides overlap by 11 amino acids.

In some embodiments, the methods employ peptides having a length of 5-30 amino acids, overlapping by 1-20 amino acids, corresponding to all or part of a given reference antigen.

In some embodiments, the methods employ peptides having a length of 15 amino acids, overlapping by 11 amino acids, corresponding to all a given reference antigen. Mixtures of such peptides may be referred to herein as "pepmix peptide pools" or "pepmixes" for a given antigen.

For example, "EBNA1 pepmix" used in Example 1 herein refers to a pool of 158, 15mer peptides overlapping by 11 amino acids, spanning the full length of the amino acid sequence for EBNA1 as shown in UniProt: P03211-1, v1.

In some embodiments in accordance with various aspects of the present disclosure, "peptides corresponding to" a given EBV antigen may be pepmix for the antigen.

Methods for Generating/Expanding Populations of Immune Cells Specific for EBV

Aspects of the present disclosure concern generating/expanding populations of immune cells specific for EBV.

An "immune cell specific for EBV" expresses/comprises a receptor (preferably a T cell receptor) capable of recognising a peptide of an antigen of EBV (e.g. when presented by an MHC molecule). EBV-specific immune cells may express/comprise such a receptor as a result of expression of endogenous nucleic acid encoding such antigen receptor, or as a result of having been engineered to express such a receptor.

The immune cells may be a cell of hematopoietic origin, e.g. a neutrophil, eosinophil, basophil, dendritic cell, lymphocyte, or monocyte. A lymphocyte may be e.g. a T cell, B cell, NK cell, NKT cell or innate lymphoid cell (ILC), or a precursor thereof. The immune cell may express e.g. CD3 polypeptides (e.g. CD3γ CD3ε, CD3ζ or CD3δ), TCR polypeptides (TCRα or TCRβ), CD27, CD28, CD4 or CD8.

Methods for generating/expanding populations of virus-specific immune cells in vitro/ex vivo are well known to the skilled person. Typical culture conditions (i.e. cell culture media, additives, temperature, gaseous atmosphere), cell numbers, culture periods, etc. can be determined by reference e.g. to Ngo et al., J Immunother. (2014) 37(4):193-203, which is hereby incorporated by reference in its entirety.

Conveniently, cultures of cells according to the present disclosure may be maintained at 37° C. in a humidified atmosphere containing 5% $CO_2$. The cells of cell cultures according to the present disclosure can be established and/or maintained at any suitable density, as can readily be determined by the skilled person. For example, cultures may be established at an initial density of ~0.5×10$^6$ to ~5×10$^6$ cells/ml of the culture (e.g. ~1×10$^6$ cells/ml).

Cultures can be performed in any vessel suitable for the volume of the culture, e.g. in wells of a cell culture plate, cell culture flasks, a bioreactor, etc. In some embodiments cells are cultured in a bioreactor, e.g. a bioreactor described in Somerville and Dudley, Oncoimmunology (2012) 1(8): 1435-1437, which is hereby incorporated by reference in its entirety. In some embodiments cells are cultured in a GRex cell culture vessel, e.g. a GRex flask or a GRex 100 bioreactor.

The methods generally comprise culturing populations of immune cells (e.g. heterogeneous populations of immune cells (e.g. peripheral blood mononuclear cells; PBMCs) comprising cells having antigen-specific receptors in the presence of antigen-presenting cells (APCs) presenting viral antigen peptide:MHC complexes, under conditions providing appropriate costimulation and signal amplification so as to cause activation and expansion. The process of T cell activation is well known to the skilled person and described in detail, for example, in Immunobiology, 5th Edn. Janeway C A Jr, Travers P, Walport M, et al. New York: Garland Science (2001), Chapter 8, which is incorporated by reference in its entirety.

Specifically, the methods involve steps in which T cells comprising T cell receptors (TCRs) specific for EBV antigen peptide:MHC complex are stimulated by APCs presenting the EBV antigen peptide:MHC complex for which the TCR is specific. The APCs are infected with virus encoding, or comprise/express the EBV antigen/peptide(s), and present the EBV antigen peptide in the context of an MHC molecule. Stimulation causes T cell activation, and promotes cell division (proliferation), resulting in generation and/or expansion of a population of T cells specific for the EBV antigen.

The population of cells obtained following stimulation is enriched for T cells specific for the EBV antigen as compared to the population prior to stimulation (i.e. the EBV antigen-specific T cells are present at an increased frequency in the population following stimulation). In this way, a population of T cells specific for the EBV antigen is expanded/generated out of a heterogeneous population of T cells having different specificities. A population of T cells specific for an EBV antigen may be generated from a single T cell by stimulation and consequent cell division. An existing population of T cells specific for an EBV antigen may be expanded by stimulation and consequent cell division of cells of the population of EBV antigen-specific T cells.

It will be appreciated that in embodiments of the various aspects of the present disclosure, the immune cells specific for EBV antigens herein are preferably T cells. In some embodiments, the T cell is a CD3+, CD4+ T cell. In some embodiments, the T cell is a CD3+, CD8+ T cell. In some embodiments, the T cell is a T helper cell ($T_H$ cell). In some embodiments, the T cell is a cytotoxic T cell (e.g. a cytotoxic T lymphocyte (CTL)). The immune cells preferably express/comprise a TCR specific for a peptide of an antigen of EBV.

An EBV-specific T cell may display certain functional properties of a T cell in response to the viral antigen for which the T cell is specific, or in response a cell comprising/expressing the virus/antigen. In some embodiments, the properties are functional properties associated with effector T cells, e.g. cytotoxic T cells.

In some embodiments, an EBV-specific T cell may display one or more of the following properties: cytotoxicity to a cell comprising/expressing EBV or the EBV antigen for which the T cell is specific; proliferation, IFNγ expression, CD107a expression, IL-2 expression, TNFα expression, perforin expression, granzyme expression, granulysin expression, and/or FAS ligand (FASL) expression in response to a cell comprising/expressing EBV or the EBV antigen for which the T cell is specific.

EBV-specific T cells express/comprise a TCR capable of recognising a peptide of the EBV antigen for which the T cell is specific when presented by the appropriate MHC molecule. EBV-specific T cells may be CD4+ T cells and/or CD8+ T cells.

The methods of the present disclosure comprise stimulating immune cells specific for an EBV antigen by contacting populations of immune cells with peptide(s) corresponding to EBV antigen(s) or APCs presenting peptide(s) corresponding to EBV antigen(s). Such method steps may be referred to herein as "stimulations" or "stimulation steps". Such method steps typically involve maintenance of the cells in culture in vitro/ex vivo, and may be referred to as "stimulation cultures".

In some embodiments, the methods comprise one or more additional stimulation steps. That is, in some embodiments the methods comprise one or more further steps of re-stimulating the cells obtained by a stimulation step. Such further stimulation steps may be referred to herein as "re-stimulations" or "re-stimulation steps". Such method steps typically involve maintenance of the cells in culture in vitro/ex vivo, and may be referred to as "re-stimulation cultures".

It will be appreciated that "contacting" PBMCs (for stimulations) or populations of cells obtained by stimulation step described herein (for re-stimulations) with peptide(s) corresponding to EBV antigen(s) generally involves culturing the PBMCs/population of cells in vitro/ex vivo in cell culture medium comprising the peptide(s). Similarly, it will be appreciated that "contacting" PBMCs/populations of cells with APCs presenting peptide(s) corresponding to EBV antigen(s) generally involves co-culturing the APCs and the PBMCs/population of cells in vitro/ex vivo in cell culture medium.

In some embodiments, the methods comprise contacting PBMCs with peptide(s) corresponding to EBV antigen(s). In such embodiments, APCs within the population of PBMCs (e.g. dendritic cells, macrophages and B cells) internalise (e.g. by phagocytosis, pinocytosis), process and present the antigens on MHC class I molecules (cross-presentation) and/or MHC class II molecules, for subsequent activation of CD8+ and/or CD4+ T cells within the population of PBMCs.

In some embodiments, the methods comprise contacting the population of cells obtained by a stimulation step described herein with peptide(s) corresponding to EBV antigen(s). In such embodiments, APCs within the population of cells (e.g. dendritic cells, macrophages and B cells) internalise (e.g. by phagocytosis, pinocytosis), process and present the antigens on MHC class I molecules (cross-presentation) and/or MHC class II molecules, for subsequent re-stimulation of CD8+ and/or CD4+ T cells within the population of cells.

In some embodiments, the methods comprise contacting PBMCs with APCs presenting peptide(s) corresponding to EBV antigen(s). In some embodiments, the methods comprise contacting the population of cells obtained by a stimulation step described herein with APCs presenting peptide(s) corresponding to EBV antigen(s).

Co-culture of T cells and APCs in stimulations and re-stimulations according to the disclosure is performed in cell culture medium. The cell culture medium can be any cell culture medium in which T cells and APCs according can be maintained in culture in vitro/ex vivo. Culture medium suitable for use in the culture of lymphocytes is well known to the skilled person, and includes, for example, RPMI-1640 medium, AIM-V medium, Iscoves medium, etc.

In some embodiments, cell culture medium may comprise RPMI-1640 medium and/or Click's medium (also known as Eagle's Ham's amino acids (EHAA) medium). The compositions of these media are well known to the skilled person. The formulation of RPMI-1640 medium is described in e.g. Moore et al., JAMA (1967) 199:519-524, and the formulation of Click's media is described in Click et al., Cell Immunol (1972) 3:264-276. RPMI-1640 medium can be obtained from e.g. ThermoFisher Scientific, and Click's medium can be obtained from e.g. Sigma-Aldrich (Catalog No. C5572).

In some embodiments, the methods of the present disclosure involve culturing PBMCs that have been contacted with peptide(s) corresponding to EBV antigen(s), or in the presence of APCs presenting peptide(s) corresponding to EBV antigen(s), in cell culture medium comprising RPMI-1640 medium and Click's medium. In some embodiments, the methods of the present disclosure involve culturing the population of cells obtained by a stimulation step described herein that have been contacted with peptide(s) corresponding to EBV antigen(s), or in the presence of APCs presenting peptide(s) corresponding to EBV antigen(s), in cell culture medium comprising RPMI-1640 medium and Click's medium.

In some embodiments the cell culture medium comprises (by volume) 25-65% RPMI-1640 medium, and 25-65% Click's medium. In some embodiments the cell culture medium comprises 30-60% RPMI-1640 medium, and 30-60% Click's medium. In some embodiments the cell culture medium comprises 35-55% RPMI-1640 medium, and 35-55% Click's medium. In some embodiments the cell culture medium comprises 40-50% RPMI-1640 medium, and 40-50% Click's medium. In some embodiments the cell culture medium comprises 45% RPMI-1640 medium, and 45% Click's medium.

In some embodiments the cell culture medium may comprise one or more cell culture medium additives. Cell culture medium additives are well known to the skilled person, and include antibiotics (e.g. penicillin, streptomycin), serum (e.g. fetal bovine serum (FBS), bovine serum albumin (BSA)), L-glutamine, cytokines/growth factors, etc.

In some embodiments, the cell culture medium comprises (by volume) 5-20% FBS, e.g. 7.5-15% FBS, or 10% FBS. In some embodiments, the cell culture medium comprises 0.5-5% GlutaMax, e.g. 1% GlutaMax. In some embodiments, the cell culture medium comprises 0.5-5% Pen/Strep, e.g. 1% Pen/Strep.

Aspects of the present disclosure employ antigen-presenting cells (APCs) in methods for generating/expanding populations of immune cells specific for EBV.

APCs according to the present disclosure may be professional APCs. Professional APCs are specialised for presenting antigen to T cells; they are efficient at processing and presenting MHC-peptide complexes at the cell surface, and express high levels of costimulatory molecules. Professional APCs include dendritic cells (DCs), macrophages, and B cells. Non-professional APCs are other cells capable of presenting MHC-peptide complexes to T cells, in particular MHC Class I-peptide complexes to CD8+ T cells.

In some embodiments the APC is an APC capable of cross-presentation on MHC class I of antigen internalised by the APC (e.g. taken-up by endocytosis/phagocytosis). Cross-presentation on MHC class I of internalized antigens to CD8+ T cells is described e.g. in Alloatti et al., Immunological Reviews (2016), 272(1): 97-108, which is hereby incorporated by reference in its entirety. APCs capable of cross-presentation include e.g. dendritic cells (DCs), macrophages, B cells and sinusoidal endothelial cells.

As explained herein, in some embodiments APCs for stimulating immune cells specific for EBV antigen(s) are comprised within the population of cells (e.g. PBMCs) comprising the immune cells specific for EBV antigen(s), which populations of cells specific for EBV antigen(s) are to be expanded in accordance with the methods of the present disclosure. In such embodiments, APCs may be e.g. dendritic cells, macrophages, B cells or any other cell type within the population of cells which is capable of presenting antigen to immune cells specific for EBV antigen(s)

In some embodiments the methods employ APCs that have been modified to express/comprise EBV antigen(s)/peptide(s) thereof. In some embodiments, the APCs may present peptide(s) corresponding to EBV antigen(s) as a result of having been contacted with the peptide(s), and having internalised them. In some embodiments, APCs may have been "pulsed" with the peptide(s), which generally involves culturing APCs in vitro in the presence of the peptide(s), for a period of time sufficient for the APCs to internalise the peptide(s).

In some embodiments the APCs may present peptide(s) corresponding to EBV antigen(s) as a result of expression from nucleic acid encoding the antigen within the cell. APCs may comprise nucleic acid encoding EBV antigen(s) as a consequence of their having been infected with EBV (e.g. in the case of B cells, e.g. LCLs). APCs may comprise nucleic acid encoding EBV antigen(s) as a consequence of nucleic acid encoding the antigen(s) having been introduced into the cell, e.g. via transfection, transduction, electroporation, etc. Nucleic acid encoding EBV antigen(s) may be provided in a plasmid/vector.

In some embodiments, APCs employed in the methods of the present disclosure are selected from activated T cells (ATCs), dendritic cells, B cells (including e.g. LCLs), and artificial antigen presenting cells (aAPCs) such as those described in Neal et al., J Immunol Res Ther (2017) 2(1): 68-79 and Turtle and Riddell Cancer J. (2010) 16(4):374-381.

In some embodiments APCs are autologous with respect to the population of cells with which they are to be co-cultured for the generation/expansion of populations of immune cells comprising immune cells specific for EBV antigen(s). That is, in some embodiments the APCs are from (or are derived from cells obtained from) the same subject as the subject from which the population of cells with which they are to be co-cultured were obtained.

The use of polyclonal activated T cells (ATCs) as APCs and methods for preparing ATCs are described e.g. in Ngo et al., J Immunother. (2014) 37(4):193-203, incorporated by reference hereinabove. Briefly, ATCs can be generated by non-specifically activating T cells in vitro by stimulating PBMCs with agonist anti-CD3 and agonist anti-CD28 antibodies, in the presence of IL-2.

Dendritic cells may be generated according to methods well known in the art, e.g. as described in Ngo et al., J Immunother. (2014) 37(4):193-203. Dendritic cells may be prepared from monocytes which may be obtained by CD14 selection from PBMCs. The monocytes may be cultured in cell culture medium causing their differentiation to immature dendritic cells, which may comprise e.g. IL-4 and GM-CSF. Immature dendritic cells may be matured by culture in the presence of IL-6, IL-1β, TNFα, PGE2, GM-CSF and IL-4.

LCLs may be generated according to methods well known in the art, e.g. as described in Hui-Yuen et al., J Vis Exp (2011) 57: 3321, and Hussain and Mulherkar, Int J Mol Cell Med (2012) 1(2): 75-87, both hereby incorporated by reference in their entirety. Briefly, LCLs can be produced by incubation of PBMCs with concentrated cell culture supernatant of cells producing EBV, for example B95-8 cells, in the presence of cyclosporin A.

Artificial antigen presenting cells (aAPCs) include e.g. K562cs cells, which are engineered to express costimulatory molecules CD80, CD86, CD83 and 4-1BBL (described e.g. in Suhoski et al., Mol Ther. (2007) 15(5):981-8).

In some embodiments the APC is not a cell infected with EBV. In some embodiments the APC is not an EBV-infected B cell. In some embodiments the APC is not an EBV-LCL.

In some embodiments, a stimulation step comprises contacting PBMCs peptide(s) corresponding to EBV antigen(s). In some embodiments, a re-stimulation step comprises contacting immune cells specific for EBV antigen(s) with APCs presenting peptide(s) corresponding to EBV antigen(s). In some embodiments, a re-stimulation step comprises contacting immune cells specific for EBV antigen(s) with ATCs presenting peptide(s) corresponding to EBV antigen(s).

In some embodiments the methods further employ agents for enhancing costimulation in stimulations and/or re-stimulations. Such agents include e.g. cells expressing costimulatory molecules (e.g. CD80, CD86, CD83 and/or 4-1BBL), such as e.g. LCLs or K562cs cells. In some embodiments the cells expressing costimulatory molecules are HLA-negative, EBV replication-incompetent LCLs, which are also referred to as "universal LCLs" or "uLCLs". uLCLs are described e.g. in US 2018/0250379 A1.

Other examples of agents for enhancing costimulation include e.g. agonist antibodies specific for costimulatory receptors expressed by T cells (e.g. 4-1 BB, CD28, OX40, ICOS, etc.), and costimulatory molecules capable of activating costimulatory receptors expressed by T cells (e.g. CD80, CD86, CD83, 4-1BBL, OX40L, ICOSL, etc.). Such agents may be provided e.g. immobilised on beads.

In some embodiments, a re-stimulation step comprises contacting immune cells specific for EBV antigen(s) with ATCs presenting peptide(s) corresponding to EBV antigen(s) in the presence of uLCLs.

Contacting of populations of immune cells with peptide(s) corresponding to EBV antigen(s) or APCs presenting peptide(s) corresponding to EBV antigen(s) may be performed in the presence of one or more cytokines, to facilitate T cell activation and proliferation. In some embodiments stimulations are performed in the presence of one or more of IL-7, IL-15, IL-6, IL-12, IL-4, IL-2 and/or IL-21. It will be appreciated that the cytokines are added exogenously to the culture, and additional to cytokines that are produced by the cells in culture. In some embodiments the added cytokines are recombinantly-produced cytokines.

Accordingly, in some embodiments the methods of the present disclosure involve culturing PBMCs that have been contacted with peptide(s) corresponding to EBV antigen(s), or in the presence of APCs presenting peptide(s) corresponding to EBV antigen(s), in the presence of one or more of IL-7, IL-15, IL-6, IL-12, IL-4, IL-2 and/or IL-21.

In some embodiments culture is in the presence of IL-7, IL-15, IL-6, IL-12, IL-4, IL-2 and/or IL-21. In some embodiments culture is in the presence of IL-7, IL-15, IL-6 and/or IL-12. In some embodiments culture is in the presence of IL-7 and/or IL-15.

In some embodiments the final concentration of IL-7 in the culture is 1-100 ng/ml, e.g. one of 2-50 ng/ml, 5-20 ng/ml or 7.5-15 ng/ml. In some embodiments the final concentration of IL-7 in the culture is about 10 ng/ml.

In some embodiments the final concentration of IL-15 in the culture is 1-100 ng/ml, e.g. one of 2-50 ng/ml, 5-20 ng/ml or 7.5-15 ng/ml. In some embodiments the final concentration of IL-15 in the culture is about 10 ng/ml.

In some embodiments the final concentration of IL-15 in the culture is 10-1000 ng/ml, e.g. one of 20-500 ng/ml, 50-200 ng/ml or 75-150 ng/ml. In some embodiments the final concentration of IL-15 in the culture is about 100 ng/ml.

In some embodiments the final concentration of IL-6 in the culture is 10-1000 ng/ml, e.g. one of 20-500 ng/ml, 50-200 ng/ml or 75-150 ng/ml. In some embodiments the final concentration of IL-6 in the culture is about 100 ng/ml.

In some embodiments the final concentration of IL-12 in the culture is 1-100 ng/ml, e.g. one of 2-50 ng/ml, 5-20 ng/ml or 7.5-15 ng/ml. In some embodiments the final concentration of IL-12 in the culture is 10 ng/ml.

In some embodiments the final concentration of IL-7 is 1-100 ng/ml (e.g. one of 2-50 ng/ml, 5-20 ng/ml or 7.5-15 ng/ml, e.g. 10 ng/ml), and the final concentration of IL-15 is 10-1000 ng/ml (e.g. one of 20-500 ng/ml, 50-200 ng/ml or 75-150 ng/ml, e.g. about 100 ng/ml).

In some embodiments the final concentration of IL-7 is 1-100 ng/ml (e.g. one of 2-50 ng/ml, 5-20 ng/ml or 7.5-15 ng/ml, e.g. 10 ng/ml), and the final concentration of IL-15 is 10-1000 ng/ml (e.g. one of 20-500 ng/ml, 50-200 ng/ml or 75-150 ng/ml, e.g. about 100 ng/ml).

In some embodiments the final concentration of IL-7 is 1-100 ng/ml (e.g. one of 2-50 ng/ml, 5-20 ng/ml or 7.5-15 ng/ml, e.g. 10 ng/ml), the final concentration of IL-6 is 10-1000 ng/ml (e.g. one of 20-500 ng/ml, 50-200 ng/ml or 75-150 ng/ml, e.g. about 100 ng/ml), the final concentration of IL-12 is 1-100 ng/ml (e.g. one of 2-50 ng/ml, 5-20 ng/ml or 7.5-15 ng/ml, e.g. 10 ng/ml), and the final concentration of IL-15 is 1-100 ng/ml (e.g. one of 2-50 ng/ml, 5-20 ng/ml or 7.5-15 ng/ml, e.g. 10 ng/ml).

In some embodiments the final concentration of IL-7 in a stimulation culture is 1-100 ng/ml (e.g. one of 2-50 ng/ml, 5-20 ng/ml or 7.5-15 ng/ml, e.g. 10 ng/ml), and the final concentration of IL-15 in a stimulation culture is 10-1000 ng/ml (e.g. one of 20-500 ng/ml, 50-200 ng/ml or 75-150 ng/ml, e.g. about 100 ng/ml).

In some embodiments the final concentration of IL-7 in a stimulation culture is 1-100 ng/ml (e.g. one of 2-50 ng/ml, 5-20 ng/ml or 7.5-15 ng/ml, e.g. 10 ng/ml), the final concentration of IL-6 in a stimulation culture is 10-1000 ng/ml (e.g. one of 20-500 ng/ml, 50-200 ng/ml or 75-150 ng/ml, e.g. about 100 ng/ml), the final concentration of IL-12 in a stimulation culture is 1-100 ng/ml (e.g. one of 2-50 ng/ml, 5-20 ng/ml or 7.5-15 ng/ml, e.g. 10 ng/ml), and the final concentration of IL-15 in a stimulation culture is 1-100 ng/ml (e.g. one of 2-50 ng/ml, 5-20 ng/ml or 7.5-15 ng/ml, e.g. 10 ng/ml).

In some embodiments the final concentration of IL-7 in a re-stimulation culture is 1-100 ng/ml (e.g. one of 2-50 ng/ml, 5-20 ng/ml or 7.5-15 ng/ml, e.g. 10 ng/ml), and the final concentration of IL-15 in a re-stimulation culture is 10-1000 ng/ml (e.g. one of 20-500 ng/ml, 50-200 ng/ml or 75-150 ng/ml, e.g. about 100 ng/ml).

Stimulations and re-stimulations according to the present methods typically involve co-culture of T cells and APCs for a period of time sufficient for APCs to stimulate the T cells, and for the T cells to undergo cell division.

In some embodiments, the methods of the present disclosure involve culturing PBMCs that have been contacted with peptide(s) corresponding to EBV antigen(s), or in the presence of APCs presenting peptide(s) corresponding to EBV antigen(s), for a period of one of at least 1 hour, 6 hours, 12 hours, 24 hours, 48 hours, 72 hours, 4 days, 5 days, 6 days, or at least 7 days. In some embodiments, culture is for a period of 24 hours to 20 days, e.g. one of 48 hours to 14 days, 3 days to 12 days, 4 to 11 days, or 6 to 10 days or 7 to 9 days.

In some embodiments, the methods of the present disclosure involve culturing the population of cells obtained by a stimulation step described herein that have been contacted with peptide(s) corresponding to EBV antigen(s), or in the presence of APCs presenting peptide(s) corresponding to EBV antigen(s), for a period of one of at least 1 hour, 6 hours, 12 hours, 24 hours, 48 hours, 72 hours, 4 days, 5 days, 6 days, or at least 7 days. In some embodiments, culture is for a period of 24 hours to 20 days, e.g. one of 48 hours to 14 days, 3 days to 12 days, 4 to 11 days, or 6 to 10 days or 7 to 9 days.

Stimulations and re-stimulations may be ended by separating the cells in culture from the media in which they have been cultured, or diluting the culture, e.g. by the addition of cell culture medium. In some embodiments, the methods comprise a step of collecting the cells at the end of the stimulation or re-stimulation culture.

In some embodiments, a re-stimulation step according to the present disclosure may be established by adding cell culture medium (and any other additives as described herein) in an amount appropriate to achieve the desired percentages/concentrations of cell culture medium, conditioned media (and any additives) for the re-stimulation step.

At the end of the culture period of a given stimulation or re-stimulation step, the cells may be collected and separated from the cell culture supernatant. The cells may be collected by centrifugation, and the cell culture supernatant may be separated from the cell pellet. The cell pellet may then be re-suspended in cell culture medium, e.g. for a re-stimulation step. In some embodiments, the cells may undergo a washing step after collection. A washing step may comprise re-suspending the cell pellet in isotonic buffer such as phosphate-buffered saline (PBS), collecting the cells by centrifugation, and discarding the supernatant.

Methods for generating and/or expanding a populations of immune cells specific for EBV antigen(s) according to the present disclosure typically involve more than a single stimulation step. There is no upper limit to the number of stimulation steps which may be performed in a method according to the present disclosure. In some embodiments the methods comprise more than 2, 3, 4 or 5 stimulation steps. In some embodiments, the methods comprise one of 2, 3, 4, 5, 6, 7, 8, 9, 10, 11, 12, 13, 14, or 15 stimulation steps. The stimulation steps in a method according to the present disclosure may be different to one another.

In some embodiments, the PBMCs employed in the methods of the disclosure are depleted of CD45RA-positive cells. That is, in some embodiments, the PBMCs are "CD45RA-positive cell-depleted PBMCs", or are "CD45RA-negative PBMCs". Depletion of CD45RA-positive cells is intended to reduce the number of NK cells and/or regulatory T cells in the populations of cells generated/expanded according to the methods of the disclosure.

In some embodiments, the methods comprise a step of depleting PBMCs of CD45RA-positive cells, e.g. prior to a stimulation step according to the disclosure. In some embodiments, the methods comprise a step of depleting the cells obtained by a stimulation step according to the present disclosure of CD45RA-positive cells, e.g. prior to a re-stimulation step according to the disclosure. Depletion of CD45RA-positive cells can be achieved by any suitable method, such as by MACS, for example using Miltenyi® Biotec columns and magnetic anti-CD45RA antibody-coated beads.

In some embodiments, the population of cells used to derive APCs employed in the methods of the disclosure is depleted of CD45RA-positive cells. That is, in some embodiments, the population of cells used to derive APCs is a "CD45RA-positive cell-depleted" or "CD45RA-negative" population. For example, in embodiments wherein ATCs are employed as APCs, the ATCs may be derived from a population of CD45RA-positive cell-depleted PBMCs, or from a population of CD45RA-negative PBMCs.

In some embodiments the methods further comprise modification of the immune cells specific for EBV antigen(s) to increase IL-7-mediated signalling in the cells. IL-7-mediated signalling has been shown to increases the survival and anti-tumor activity of tumor-specific T cells—see e.g. in Shum et al., Cancer Discov. (2017) 7(11):1238-1247, and WO 2018/038945 A1.

Particular Exemplary Embodiments of Method Steps

The following particular exemplary method steps are expressly contemplated in connection with the present disclosure:

(A) Stimulating immune cells specific for an EBV lytic antigen by contacting PBMCs with BZLF1 pepmix, BRLF1 pepmix, BMRF1 pepmix, BMLF1 pepmix, BALF2 pepmix, BNLF2A pepmix, BNLF2B pepmix and/or BMRF2 pepmix.

(B) Stimulating immune cells specific for an EBV lytic antigen by contacting PBMCs with BZLF1 pepmix, BRLF1 pepmix, BMRF1 pepmix, BMLF1 pepmix, BXLF1 pepmix, BALF1 pepmix, BLLF2 pepmix, BALF2 pepmix and/or BNLF2A pepmix.

(C) Stimulating immune cells specific for an EBV lytic antigen by contacting PBMCs with BZLF1 pepmix, BRLF1 and/or BMRF1 pepmix.

(D) Stimulating immune cells specific for an EBV lytic antigen by contacting PBMCs with BMRF1 pepmix, BMLF1 pepmix, BALF2 pepmix, BNLF2A pepmix, BNLF2B pepmix and/or BMRF2 pepmix.

(E) Stimulating immune cells specific for an EBV lytic antigen and immune cells specific for an EBV latent antigen by contacting PBMCs with:

BZLF1 pepmix, BRLF1 pepmix, BMRF1 pepmix, BMLF1 pepmix, BALF2 pepmix, BNLF2A pepmix, BNLF2B pepmix and/or BMRF2 pepmix; and EBNA1 pepmix, LMP1 pepmix and/or LMP2 pepmix.

(F) Stimulating immune cells specific for an EBV lytic antigen and immune cells specific for an EBV latent antigen by contacting PBMCs with:

BZLF1 pepmix, BRLF1 pepmix, BMRF1 pepmix, BMLF1 pepmix, BXLF1 pepmix, BALF1 pepmix, BLLF2 pepmix, BALF2 pepmix and/or BNLF2A pepmix; and EBNA1 pepmix, LMP1 pepmix and/or LMP2 pepmix.

(G) Stimulating immune cells specific for an EBV lytic antigen and immune cells specific for an EBV latent antigen by contacting PBMCs with:

BZLF1 pepmix, BRLF1 pepmix and/or BMRF1 pepmix; and

EBNA1 pepmix, LMP1 pepmix and/or LMP2 pepmix.

(H) Stimulating immune cells specific for an EBV lytic antigen and immune cells specific for an EBV latent antigen by contacting PBMCs with:
   BMRF1 pepmix, BMLF1 pepmix, BALF2 pepmix, BNLF2A pepmix, BNLF2B pepmix and/or BMRF2 pepmix; and
   EBNA1 pepmix, LMP1 pepmix and/or LMP2 pepmix.

(I) Stimulating immune cells according to any one of (A) to (H), in the presence of IL-7, IL-15, IL-6 and/or IL-12.

(J) Stimulating immune cells according to any one of (A) to (I), in the presence of IL-7 and/or IL-15.

(K) Stimulating immune cells according to any one of (A) to (J) wherein the PBMCs are depleted of CD45RA-positive cells.

(L) Stimulating immune cells specific for an EBV lytic antigen by co-culture with APCs which have been pulsed with BZLF1 pepmix, BRLF1 pepmix, BMRF1 pepmix, BMLF1 pepmix, BALF2 pepmix, BNLF2A pepmix, BNLF2B pepmix and/or BMRF2 pepmix.

(M) Stimulating immune cells specific for an EBV lytic antigen by co-culture with APCs which have been pulsed with BZLF1 pepmix, BRLF1 pepmix, BMRF1 pepmix, BMLF1 pepmix, BXLF1 pepmix, BALF1 pepmix, BLLF2 pepmix, BALF2 pepmix and/or BNLF2A pepmix.

(N) Stimulating immune cells specific for an EBV lytic antigen by co-culture with APCs which have been pulsed with BZLF1 pepmix, BRLF1 and/or BMRF1 pepmix.

(O) Stimulating immune cells specific for an EBV lytic antigen by co-culture with APCs which have been pulsed with BMRF1 pepmix, BMLF1 pepmix, BALF2 pepmix, BNLF2A pepmix, BNLF2B pepmix and/or BMRF2 pepmix.

(P) Stimulating immune cells specific for an EBV lytic antigen and immune cells specific for an EBV latent antigen by co-culture with APCs which have been pulsed with:
   BZLF1 pepmix, BRLF1 pepmix, BMRF1 pepmix, BMLF1 pepmix, BALF2 pepmix, BNLF2A pepmix, BNLF2B pepmix and/or BMRF2 pepmix; and
   EBNA1 pepmix, LMP1 pepmix and/or LMP2 pepmix.

(Q) Stimulating immune cells specific for an EBV lytic antigen and immune cells specific for an EBV latent antigen by co-culture with APCs which have been pulsed with:
   BZLF1 pepmix, BRLF1 pepmix, BMRF1 pepmix, BMLF1 pepmix, BXLF1 pepmix, BALF1 pepmix, BLLF2 pepmix, BALF2 pepmix and/or BNLF2A pepmix; and
   EBNA1 pepmix, LMP1 pepmix and/or LMP2 pepmix.

(R) Stimulating immune cells specific for an EBV lytic antigen and immune cells specific for an EBV latent antigen by co-culture with APCs which have been pulsed with:
   BZLF1 pepmix, BRLF1 pepmix and/or BMRF1; and
   EBNA1 pepmix, LMP1 pepmix and/or LMP2 pepmix.

(S) Stimulating immune cells specific for an EBV lytic antigen and immune cells specific for an EBV latent antigen by co-culture with APCs which have been pulsed with:
   BMRF1 pepmix, BMLF1 pepmix, BALF2 pepmix, BNLF2A pepmix, BNLF2B pepmix and/or BMRF2 pepmix; and
   EBNA1 pepmix, LMP1 pepmix and/or LMP2 pepmix.

(T) Stimulating immune cells according to any one of (L) to (S), wherein the APCs are ATCs.

(U) Stimulating immune cells according to (T), wherein the ATCs are derived from PBMCs depleted of CD45RA-positive cells.

(V) Stimulating immune cells according to any one of (L) to (U), in the presence of uLCLs.

(W) Stimulating immune cells according to any one of (L) to (V), in the presence of IL-7 and/or IL-15.

(X) Stimulating immune cells according to any one of (A) to (K), and subsequently stimulating immune cells according to any one of (L) to (W).

Properties of the Methods/Populations of Immune Cells Generated/Expanded by the Methods The methods of the present disclosure may optionally be characterised by reference to properties of the methods, and/or properties of the populations of immune cells generated/expanded by the methods.

In some embodiments, a population of immune cells generated/expanded in accordance with the methods of the present disclosure possess one or more of the following properties:
   a) comprises cells which produce IFNγ in response to stimulation with peptide(s) corresponding to one or more EBV lytic antigens;
   b) comprises cells which produce IFNγ in response to stimulation with peptide(s) corresponding to one or more EBV lytic antigens, and comprises cells which produce IFNγ in response to stimulation with peptide(s) corresponding to one or more EBV latent antigens;
   c) comprises cells which produce IFNγ in response to stimulation with EBV-infected cells;
   d) cytolytic activity against autologous EBV-infected cells;
   e) anticancer activity against EBV-positive cancer in vivo;
   f) inhibition of growth of an EBV-positive tumor in vivo; and
   g) reduction of metastasis of EBV-positive cancer in vivo.

Populations of immune cells may be evaluated for whether they comprise cells which to produce IFNγ in response to stimulation with peptide(s) corresponding to EBV antigens and/or EBV-infected cells (e.g. LCLs) e.g. by ELISPOT analysis, which may be performed e.g. as described in Example 2.

Populations of immune cells may be evaluated for cytolytic activity against autologous EBV-infected cells using the methods reviewed in Zaritskaya et al., Expert Rev Vaccines (2011), 9(6):601-616, hereby incorporated by reference in its entirety, such as $^{51}$Cr release assay. Analysis may be performed using autologous EBV-LCLs, e.g. as described in Example 3.

Populations of immune cells may be evaluated in vivo for anticancer activity against EBV-positive cancer and/or inhibition of tumor growth of an EBV-positive tumor by analysis in an appropriate model. Suitable models and analysis include the EBV-LCL xenograft model methods employed in Example 4. Metastasis can be evaluated e.g. by monitoring the location of cancerous cells within the animal in such a model, e.g. as performed in Example 4.

In some embodiments, a population of immune cells generated/expanded in accordance with the methods of the present disclosure may possess one or more of the following, as compared to a population of immune cells generated/expanded according to a reference method for generating/expanding EBV-specific immune cells:
   h) comprises a greater number/proportion of cells which produce IFNγ in response to stimulation with peptide(s) corresponding to one or more EBV antigen(s);
   i) comprises a greater number/proportion of cells which produce IFNγ in response to stimulation with peptide(s) corresponding to one or more EBV lytic antigen(s);
   j) comprises cells specific for a larger number of different EBV antigens (i.e. a wider range of EBV antigens);

k) comprises a greater number/proportion of cells which produce IFNγ in response to stimulation with EBV-infected cells;
l) greater anticancer activity against EBV-positive cancer in vivo;
m) greater inhibition of growth of an EBV-positive tumor in vivo;
n) greater reduction of metastasis of EBV-positive cancer in vivo;
o) greater persistence in vivo; and
p) elicits the production of an increased amount of one or more proinflammatory cytokine(s) (e.g. GM-CSF and/or IFNγ) in a subject administered with the population of immune cells.
p) elicits the production of a reduced production of one or more anti-inflammatory cytokines (e.g. IL-10) in a subject administered with the population of immune cells.

Survival/persistence of a given population of immune cells in vivo can be evaluated e.g. using methods in which cells are labelled with a detectable marker or reporter, and their survival is monitored over time. Such methods include e.g. labelling cells with firefly luciferase, and measuring activity at different time points.

Production of cytokines by a subject administered with a given population of immune cells can be evaluated e.g. by analysis of a blood-derived sample (e.g. whole blood, plasma, serum) obtained from the subject. Cytokine levels can be determined e.g. by ELISA, e.g. as described in Example 4.

A reference method for generating/expanding EBV-specific immune cells may be a method as described in Example 1 herein employing latent pepmixes (only) in stimulations.

Methods Using Populations of Immune Cells Generated/Expanded by the Methods

The populations of immune cells comprising EBV-specific immune cells generated/expanded as described herein find use in therapeutic and/or prophylactic methods.

A method for treating/preventing a disease/condition in a subject is provided, comprising administering a population of immune cells specific for EBV generated/expanded according to a method of the present disclosure to a subject. Also provided is a population of immune cells specific for EBV generated/expanded according to a method of the present disclosure for use in a method of medical treatment/prophylaxis. Also provided is a population of immune cells generated/expanded according to a method of the present disclosure for use in a method for treating/preventing a disease/condition. Also provided is the use of a population of immune cells specific for EBV generated/expanded according to a method of the present disclosure in the manufacture of a medicament for use in a method for treating/preventing a disease/condition.

In particular, use of populations of immune cells specific for EBV generated/expanded according to the present disclosure in methods to treat/prevent diseases/conditions by adoptive cell transfer (ACT) is contemplated.

Adoptive cell transfer generally refers to a process by which cells (e.g. immune cells) are obtained from a subject, typically by drawing a blood sample from which the cells are isolated. The cells are then typically modified and/or expanded, and then administered either to the same subject (in the case of adoptive transfer of autologous/autogenic cells) or to a different subject (in the case of adoptive transfer of allogeneic cells). The treatment is typically aimed at providing a population of cells with certain desired characteristics to a subject, or increasing the frequency of such cells with such characteristics in that subject. Adoptive transfer may be performed with the aim of introducing a cell or population of cells into a subject, and/or increasing the frequency of a cell or population of cells in a subject.

Adoptive transfer of immune cells is described, for example, in Kalos and June 2013, Immunity 39(1): 49-60, and Davis et al. 2015, Cancer J. 21(6): 486-491, both of which are hereby incorporated by reference in their entirety. The skilled person is able to determine appropriate reagents and procedures for adoptive transfer of cells according to the present disclosure, for example by reference to Dai et al., 2016 J Nat Cancer Inst 108(7): djv439, which is incorporated by reference in its entirety.

In some embodiments, the methods comprise:
(a) generating/expanding a population of immune cells specific for EBV in accordance with the methods of the present disclosure, and
(b) administering the generated/expanded population of immune cells specific for EBV to a subject.

In some embodiments, the methods comprise:
(a) isolating/obtaining a population of immune cells (e.g. PBMCs) from a subject;
(b) generating/expanding a population of immune cells specific for EBV in accordance with the methods of the present disclosure, and
(c) administering the generated/expanded population of immune cells specific for EBV to a subject.

In some embodiments, the subject from which the immune cells (e.g. PBMCs) are isolated is the same subject to which the generated/expanded population of immune cells specific for EBV is administered (i.e., adoptive transfer may be of autologous/autogenic cells). In some embodiments, the subject from which the immune cells (e.g. PBMCs) are isolated is a different subject to the subject to which the generated/expanded population of immune cells specific for EBV is administered (i.e., adoptive transfer may be of allogeneic cells).

In some embodiments the methods may comprise one or more of:
taking a blood sample from a subject;
isolating immune cells (e.g. PBMCs) from the blood sample;
generating/expanding a population of immune cells specific for EBV in accordance with the methods of the present disclosure;
collecting/isolating the population of immune cells specific for EBV;
mixing the population of immune cells specific for EBV with an adjuvant, diluent, or carrier;
administering the population of immune cells specific for EBV to a subject.

The methods may be effective to reduce the development/progression of a disease/condition, alleviation of the symptoms of a disease/condition or reduction in the pathology of a disease/condition. The methods may be effective to prevent progression of the disease/condition, e.g. to prevent worsening of, or to slow the rate of development of, the disease/condition. In some embodiments the methods may lead to an improvement in the disease/condition, e.g. a reduction in the symptoms of the disease/condition or reduction in some other correlate of the severity/activity of the disease/condition. In some embodiments the methods may prevent development of the disease/condition a later stage (e.g. a chronic stage or metastasis).

It will be appreciated that the therapeutic and prophylactic utility of the populations of cells generated/expanded in accordance with the present disclosure extends to the treatment/prevention of any disease/condition that would derive therapeutic or prophylactic benefit from a reduction in EBV load, and/or the number/activity of cells infected with EBV.

For example, the disease/condition may be a disease/condition in which EBV or cells infected with EBV are pathologically implicated, e.g. a disease/condition in which EBV infection is positively associated with the onset, development or progression of the disease/condition, and/or severity of one or more symptoms of the disease/condition, or for which EBV infection is a risk factor for the onset, development or progression of the disease/condition.

The treatment may be aimed at one or more of: reducing the EBV load, reducing the number/proportion of EBV-positive cells, reducing the activity of EBV-positive cells, delaying/preventing the onset/progression of symptoms of the disease/condition, reducing the severity of symptoms of the disease/condition, reducing the survival/growth of EBV-positive cells, increasing survival of the subject.

In some embodiments, the disease/condition to be treated/prevented in accordance with the present disclosure is a disease/condition characterised by EBV infection.

In some embodiments, a subject may be selected for treatment described herein based on the detection of EBV/cells infected with EBV, e.g. in the periphery, or in an organ/tissue which is affected by the disease/condition (e.g. an organ/tissue in which the symptoms of the disease/condition manifest), or by the detection of EBV-positive cancer cells (e.g. EBV-positive cells in a tumor). The disease/condition may affect any tissue or organ or organ system. In some embodiments the disease/condition may affect several tissues/organs/organ systems.

In some embodiments a subject may be selected for therapy/prophylaxis in accordance with the present disclosure based on determination that the subject is infected with EBV or comprises cells infected with EBV.

EBV is implicated in several cancers, as reviewed e.g. in Jha et al., Front Microbiol. (2016) 7:1602, which is hereby incorporated by reference in its entirety.

Accordingly, in some embodiments, the disease to be treated/prevented in accordance with the present disclosure is a cancer.

Cancer may refer to any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, and/or white blood cells.

Tumors may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, hematologic cancer and sarcoma.

In some embodiments the cancer is selected from the group consisting of: colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer or mesothelioma.

In some embodiments the cancer to be treated/prevented is an EBV-associated cancer. "EBV-associated" cancers may be a cancers which are caused or exacerbated by infection with EBV, cancers for which infection is a risk factor and/or cancers for which infection is positively associated with onset, development, progression, severity or metastasis.

EBV-associated cancers which may be treated/prevented in accordance with the present disclosure include B cell-associated cancers such as Burkitt's lymphoma, post-transplant lymphoproliferative disease (PTLD), central nervous system lymphoma (CNS lymphoma), Hodgkin's lymphoma, non-Hodgkin's lymphoma, and EBV-associated lymphomas associated with immunodeficiency (including e.g. EBV-positive lymphoma associated with X-linked lymphoproliferative disorder, EBV-positive lymphoma associated with HIV infection/AIDS, and oral hairy leukoplakia), and epithelial cell related cancers such as nasopharyngeal carcinoma (NPC) and gastric carcinoma (GC).

In some embodiments the cancer is selected from lymphoma (e.g. EBV-positive lymphoma), head and neck squamous cell carcinoma (HNSCC; e.g. EBV-positive HNSCC), nasopharyngeal carcinoma (NPC; e.g. EBV-positive NPC), and gastric carcinoma (GC; e.g. EBV-positive GC).

EBV-infection is also implicated in the development/progression of a variety of autoimmune diseases such as multiple sclerosis and systemic lupus erythematosus (SLE; see e.g. Ascherio and Munger Curr Top Microbiol Immunol. (2015); 390(Pt 1):365-85), and EBV antigen EBNA2 has recently been shown to associate with genetic regions implicated as risk factors for the development of SLE, multiple sclerosis, rheumatoid arthritis, inflammatory bowel disease, type 1 diabetes, juvenile idiopathioc arthritis and celiac disease (Harley et al., Nat Genet. (2018) 50(5): 699-707).

Accordingly, in some embodiments the disease/condition to be treated/prevented in accordance with the present disclosure is selected from SLE, multiple sclerosis, rheumatoid arthritis, inflammatory bowel disease, type 1 diabetes, juvenile idiopathioc arthritis and celiac disease.

Subjects

The subject in accordance with aspects the disclosure described herein may be any animal or human. The subject is preferably mammalian, more preferably human. The subject may be a non-human mammal, but is more preferably human. The subject may be any gender. The subject may be a patient. A subject may have been diagnosed with a disease/condition requiring treatment, may be suspected of having such a disease/condition, or may be at risk of developing/contracting such a disease/condition.

In embodiments according to the present disclosure the subject is preferably a human subject. In some embodiments, the subject to be treated according to a therapeutic or prophylactic method of the disclosure herein is a subject having, or at risk of developing, a disease/condition. In embodiments according to the present disclosure, a subject may be selected for treatment according to the methods based on characterisation for certain markers of such a disease/condition.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMC Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Numbered Paragraphs

The following numbered paragraphs (paras) provide further statements of features and combinations of features which are contemplated in connection with the present disclosure:

1. A method for generating or expanding a population of immune cells comprising immune cells specific for an Epstein Barr Virus (EBV) lytic antigen, comprising stimulating immune cells specific for an EBV lytic antigen by contacting peripheral blood mononuclear cells (PBMCs) with: (i) one or more peptides corresponding to all or part of one or more EBV lytic antigens; or (ii) antigen presenting cells (APCs) presenting one or more peptides corresponding to all or part of one or more EBV lytic antigens.

2. The method according to para 1, wherein the method further comprises re-stimulating the immune cells specific for an EBV lytic antigen by contacting them with APCs presenting one or more peptides corresponding to all or part of one or more EBV lytic antigens.

3. A method for generating or expanding a population of immune cells comprising immune cells specific for an Epstein Barr Virus (EBV) lytic antigen and immune cells specific for an EBV latent antigen, comprising stimulating immune cells specific for an EBV lytic antigen and immune cells specific for an EBV latent antigen by contacting peripheral blood mononuclear cells (PBMCs) with: (i) one or more peptides corresponding to all or part of one or more EBV lytic antigens, and one or more peptides corresponding to all or part of one or more EBV latent antigens; or (ii) antigen presenting cells (APCs) presenting one or more peptides corresponding to all or part of one or more EBV lytic antigens, and one or more peptides corresponding to all or part of one or more EBV latent antigens.

4. The method according to para 3, wherein the method further comprises re-stimulating the immune cells specific for an EBV lytic antigen and the immune cells specific for an EBV latent antigen by contacting them with APCs presenting one or more peptides corresponding to all or part of one or more EBV lytic antigens, and one or more peptides corresponding to all or part of an EBV latent antigen.

5. The method according to any one of paras 1 to 4, wherein the one or more EBV lytic antigens are selected from BZLF1, BRLF1, BMLF1, BMRF1, BXLF1, BALF1, BALF2, BGLF5, BHRF1, BNLF2A, BNLF2B, BHLF1, BLLF2, BKRF4, BMRF2, BALF4, BILF1, BILF2, BNFR1, BVRF2, BALF3, BALF5 and BDLF3.

6. The method according to any one of paras 1 to 5, wherein the one or more EBV lytic antigens are selected from BZLF1, BRLF1, BMLF1, BMRF1, BALF2, BNLF2A, BNLF2B, BMRF2 and BDLF3.

7. The method according to any one of paras 3 to 6, wherein the one or more EBV latent antigens are selected from EBNA1, EBNA-LP, EBNA2, EBNA3A, EBNA3B, EBNA3C, BARF1, LMP1, LMP2A and LMP2B.

8. The method according to any one of paras 3 to 7, wherein the one or more EBV latent antigens are selected from EBNA1, LMP1, LMP2A and LMP2B.

9. The method according to any one of paras 1 to 8, wherein the PBMCs are PBMCs depleted of CD45RA-positive cells.

10. An isolated population of immune cells obtained or obtainable by a method according to any one of paras 1 to 9.

11. An isolated population of immune cells comprising immune cells specific for an Epstein Barr Virus (EBV) lytic antigen.

12. An isolated population of immune cells comprising immune cells specific for an Epstein Barr Virus (EBV) lytic antigen and immune cells specific for an EBV latent antigen.

13. A pharmaceutical composition comprising an isolated population of immune cells according to any one of paras 10 to 12.

14. An isolated population of immune cells according to any one of paras 10 to 12, or a pharmaceutical composition according to para 13, for use in a method of treatment or prevention of a disease or disorder associated with EBV infection.

15. Use of isolated population of immune cells according to any one of paras 10 to 12, or a pharmaceutical composition according to para 13, in the manufacture of a medicament for use in a method of treatment or prevention of a disease or disorder associated with EBV infection.

16. A method for treating or preventing a disease or disorder associated with EBV infection, comprising administering an isolated population of immune cells according to any one of paras 10 to 12, or a pharmaceutical composition according to para 13, to a subject.

17. An isolated population of immune cells according to any one of paras 10 to 12, or a pharmaceutical composition according to para 13, for use in a method of treatment or prevention of a cancer.

18. Use of isolated population of immune cells according to any one of paras 10 to 12, or a pharmaceutical composition according to para 13, in the manufacture of a medicament for use in a method of treatment or prevention of a cancer.

19. A method for treating or preventing a cancer, comprising administering an isolated population of immune cells according to any one of paras 10 to 12, or a pharmaceutical composition according to para 13, to a subject.

20. The isolated population of immune cells or pharmaceutical composition for use according to para 17, the use according to para 18, or the method according to para 19, wherein the cancer is an EBV-associated cancer.

21. The isolated population of immune cells or pharmaceutical composition for use, the use, or the method according to para 20, wherein the EBV-associated cancer is selected from EBV-positive lymphoma, EBV-positive nasopharyngeal carcinoma, and EBV-positive gastric carcinoma.

22. A method for killing a cell infected with EBV, comprising contacting a cell infected with EBV with an isolated population of immune cells according to any one of paras 10 to 12, or a pharmaceutical composition according to para 13.

23. Use of an isolated population of immune cells according to any one of paras 10 to 12, or a pharmaceutical composition according to para 13 to kill a cell infected with EBV.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value.

Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may be performed in vitro or in vivo. In some embodiments, methods described herein are performed in vitro. The term "in vitro" is intended to encompass experiments with cells in culture whereas the term "in vivo" is intended to encompass experiments with intact multi-cellular organisms.

BRIEF DESCRIPTION OF THE FIGURES

Embodiments and experiments illustrating the principles of methods and compositions of the disclosure will now be discussed with reference to the accompanying figures.

FIG. 1A shows the numbers of SFCs per 100,000 cells in response to stimulation with the indicated antigens, amongst EBVSTs generated by stimulations using latent pepmix (T2 EBVSTs), or latent+lytic pepmix (All-EBVSTs). FIG. 1B shows the numbers of SFCs per 100,000 cells in response to stimulation with the indicated antigens, amongst EBVSTs generated by stimulations using lytic pepmix (lytic EBVSTs), or latent+lytic pepmix (All-EBVSTs).

FIG. 6A shows tumor volume ($mm^3$) over time, and FIGS. 6B and 6C shows tumor burden over time as measured by luciferase activity of the firefly luciferase-expressing EBV-LCLs.

FIGS. 8A to 8C show tumor burden over time as measured by luciferase activity of the firefly luciferase-expressing EBV-LCLs. FIG. 8A shows the dorsal view, and FIG. 8B shows the ventral view at the indicated day relative to injection of the EBVSTs. FIG. 8C shows total tumor burden over time. FIG. 8D shows tumor volume ($mm^3$) over time.

FIG. 9A shows the level of GM-CSF, FIG. 9B shows the level of IFNγ, and FIG. 9C shows the level of IL-10. ***P=0.0001.

EXAMPLES

Figure 1A:
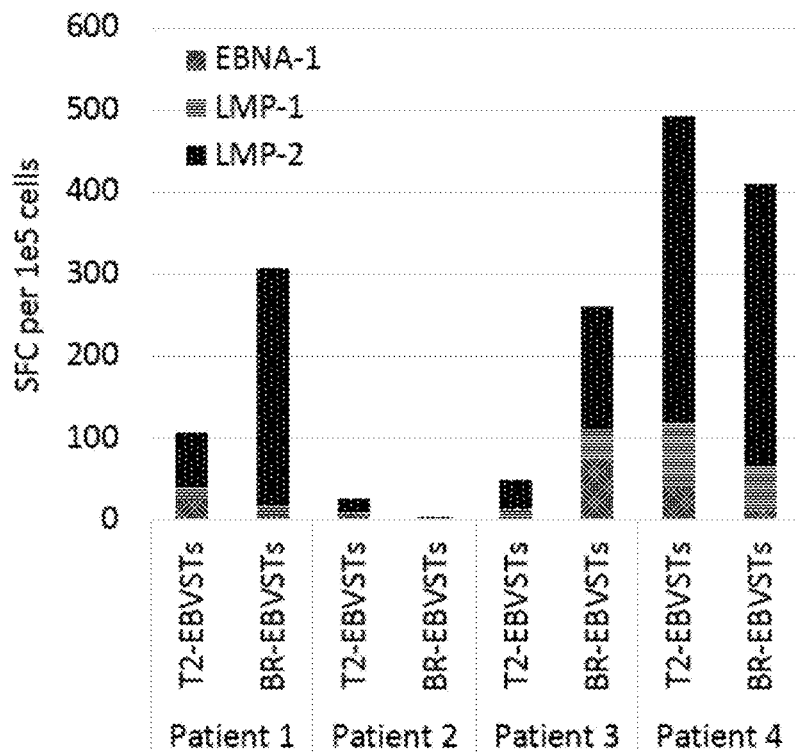
FIGS. 1A and 1B. Bar charts showing the number of spot-forming cells (SFCs) per 100,000 cells specific for the indicated EBV antigens, within populations of cells expanded from PBMCs obtained from four different EBV-positive lymphoma patients.

In the following Examples, the inventors describe the generation of populations of cells comprising EBV-specific T cells from PBMC populations, by stimulation with peptides of different EBV antigens. The inventors characterise the expanded cell populations for their EBV-reactivity, ability to display effector activity against EBV-infected cells, and their anti-cancer activity against EBV-positive cancer in vivo. The inventors also investigate methods for increasing the proportion of EBV-reactive cells in expanded populations, and their anti-cancer activity and persistence in vivo.

Example 1: Generation of EBV-Specific T Cells

Peripheral blood mononuclear cells (PBMCs) were isolated from blood samples obtained from healthy donors or lymphoma patients according to the standard Ficoll-Paque density gradient centrifugation method.
Generation of ATCs Anti-CD3 (clone OKT3) and anti-CD28 agonist antibodies were coated onto wells of tissue culture plates by addition of 0.5 ml of 1:1000 dilution of 1 mg/ml antibodies, and incubation for 2-4 hr at 37° C., or at 4° C. overnight. $1 \times 10^6$ PBMCs (in 2 ml of cell culture medium) were stimulated by culture on the anti-CD3/CD28 agonist antibody-coated plates in CTL cell culture medium (containing RPMI-1640 medium, 50% Click's medium, 10% FBS, 1% GlutaMax, 1% Pen/Strep) supplemented with 10 ng/ml IL-7 and 5 ng/ml IL-15. The cells were maintained at 37° C. in a 5% $CO_2$ atmosphere. The next day, 1 ml of the cell culture medium was replaced with fresh CTL medium containing 20 ng/ml IL-7 and 200 ng/ml IL-15. ATCs were maintained in culture, and subsequently harvested and used in experiments or cryopreserved between days 5-7.
Universal LCLs LCLs lacking surface expression of HLA class I and HLA class II (i.e. HLA-negative LCLs) were obtained by targeted knockout of genes encoding HLA class I and HLA class II molecules in cells of a lymphoblastoid cell line prepared by EBV-transformation of B cells. The HLA-negative cells were further modified to knockout genes necessary for EBV replication. The resulting cells obtained by the methods are referred to herein as universal LCLs (uLCLs).

Expansion of EBV-Specific T Cells

EBV-specific T cells were expanded by stimulating $2 \times 10^6$ PBMCs for 9 days with one of the following combinations of pepmixes obtained from JPT Technologies (overlapping 15mer amino acid peptide libraries overlapping by 11 amino acids, spanning the full amino acid sequence of the relevant antigen), in cell culture medium containing 50% Advanced RPMI, 50% Click's medium, 10% FBS, 1% GlutaMax, 1% Pen/Strep, supplemented with IL-7 (10 ng/ml) and IL-15 (100 ng/ml):

(i) EBNA1 pepmix (JPT Cat. No. PM-EBV-EBNA1)+LMP1 pepmix (JPT Cat. No. PM-EBV-LMP1)+LMP2 pepmix (JPT Cat. No. PM-EBV-LMP2)—"Latent pepmixes"

(ii) BZLF1 pepmix (JPT Cat. No. PM-EBV-BZLF1)+BRLF1 pepmix (JPT Cat. No. PM-EBV-BRLF1)+BMRF1 pepmix (JPT Cat. No. PM-EBV-BMRF1)+BMLF1 pepmix*+BALF2 pepmix*+BNLF2A pepmix*+BNLF2B pepmix*+BMRF2 pepmix*—"Lytic pepmixes"

*Pepmixes for BMLF1, BALF2, BNLF2A, BNLF2B, BMRF2 were prepared by combining individual constituent peptides obtained from Genemed.

(iii) EBNA1 pepmix+LMP1 pepmix+LMP2 pepmix+BZLF1 pepmix+BRLF1 pepmix+BMRF1 pepmix+BMLF1 pepmix+BALF2 pepmix+BNLF2A pepmix+BNLF2B pepmix+BMRF2 pepmix—"Latent+lytic pepmixes"

Combinations of pepmixes (i.e. pepmix mixtures) were used in stimulations at a final amount of 10 ng pepmix mixture per $1 \times 10^6$ PBMCs.

(iv) BZLF1 pepmix+BRLF1 pepmix+BMRF1 pepmix—"Immediate-early lytic pepmixes"

(v) BMRF1 pepmix+BMLF1 pepmix+BALF2 pepmix+BNLF2A pepmix+BNLF2B pepmix+BMRF2 pepmix (JPT Cat. No. PM-EBV-BMRF1)—"Early lytic pepmixes"

Additional cell culture medium was added as necessary over the course of the 9 days, and cytokines were replenished on day 5, 6 or 7.

At the end of the 9 day culture period, cells were re-stimulated by co-culture with irradiated, peptide-pulsed autologous activated T cells (ATCs) in the presence of uLCLs. Briefly, $2 \times 10^6$ ATCs were incubated with pepmixes (10 ng pepmix mixture per $1 \times 10^6$ ATCs) at 37° C. for 30 min in CTL medium, and subsequently irradiated at 30Gy and harvested. The peptide-pulsed ATCs were then mixed with the cells in culture and uLCLs (irradiated at 100Gy), in CTL medium containing IL-7 (10 ng/ml) and IL-15 (100 ng/ml), at a ratio of responder cells:peptide-pulsed ATCs:irradiated uLCLs of 1:1:5. Specifically, $1 \times 10^5$ responder cells, $1 \times 10^5$ peptide-pulsed ATCs and $0.5 \times 10^6$ irradiated uLCLs were cultured in 2 mL CTL medium in wells of a 24 well tissue culture plate.

Cells were maintained at 37° C. in a 5% $CO_2$ atmosphere. After 3-4 days further cell culture medium containing IL-7 (10 ng/ml) and IL-15 (100 ng/ml) was added as necessary. On day 5 or 6 further cell culture medium containing IL-7 (10 ng/ml) and IL-15 (100 ng/ml) was added as necessary, and after 6-7 days the expanded EBVSTs were harvested for analysis or use in experiments.

In instances throughout the Examples and figures:
EBVSTs generated by methods employing latent pepmixes (i.e. (i) above) are referred to as "type 2 latent antigen (T2)-EBVSTs";
EBVSTs generated by methods employing lytic pepmixes (i.e. (ii) above) are referred to as "Lytic-EBVSTs";

EBVSTs generated by methods employing latent+lytic pepmixes (i.e. (iii) above) are referred to as "broad repertoire (BR)-EBVSTs";

EBVSTs generated by methods employing immediate-early lytic pepmixes (i.e. (iv) above) are referred to as "Immediate-early (IE)-EBVSTs"; and EBVSTs generated by methods employing early lytic pepmixes (i.e. (v) above) are referred to as "early (E)-EBVSTs".

Example 2: Analysis of Specificity of EBVSTs for EBV Antigens

EBVSTs prepared from PBMCs of EBV-positive lymphoma patients using the different pepmixes were analysed by ELISPOT to determine their ability to recognise different EBV antigens.

Briefly, EBVSTs were plated at $1 \times 10^5$ cells/well in 96-well plates pre-coated with anti-IFNγ capture antibody, and stimulated with pepmixes corresponding to the indicated EBV peptides. After 18-20 hrs incubation, plates were developed for IFNγ+ spots, dried overnight at room temperature in the dark, and quantified. The frequency of T cells specific to each antigen was expressed as specific spot-forming cells (SFCs) per input cell number.

Figure 1B:
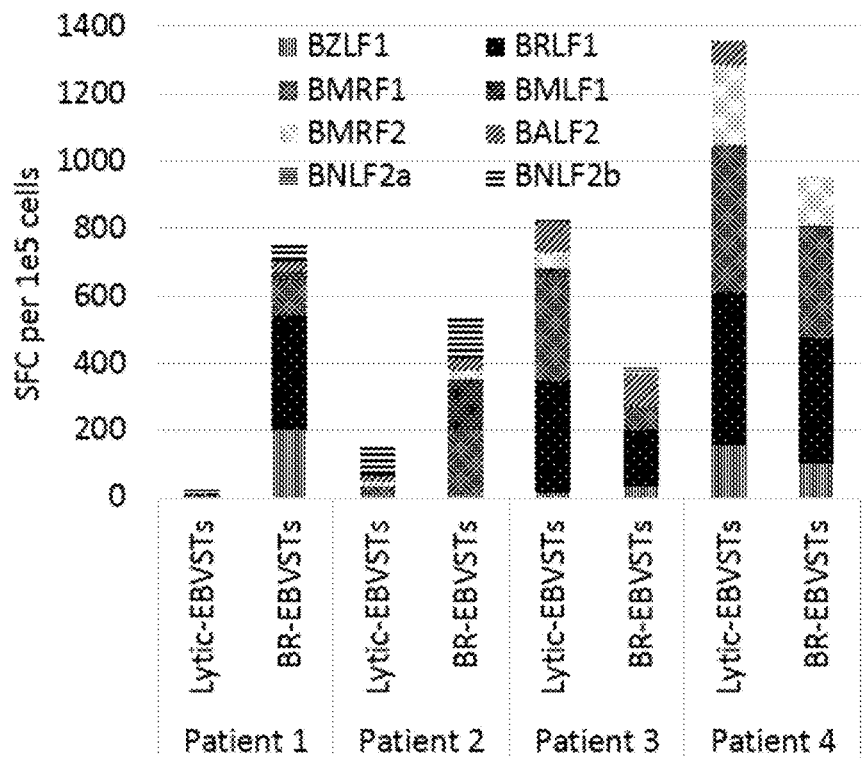

FIGS. 1A and 1B show that T-cells specific for lytic cycle antigens can be generated by stimulation with premixes for lytic cycle antigens alone. Combining the pepmixes for latent and lytic antigens did not compromise the specificity for any single antigen, and the total frequency of antigen-specific T-cells was greater when pepmixes were combined.

Some patient T-cells show poor specificity when latent antigen pepmixes or lytic antigen pepmixes are used alone, but when latent antigen pepmixes and lytic antigen pepmixes are used in combination, good specificity can be achieved (see donor 2). This is thought to result of the production of cytokines by activated T-cells, which provide help for each other.

Figure 2:
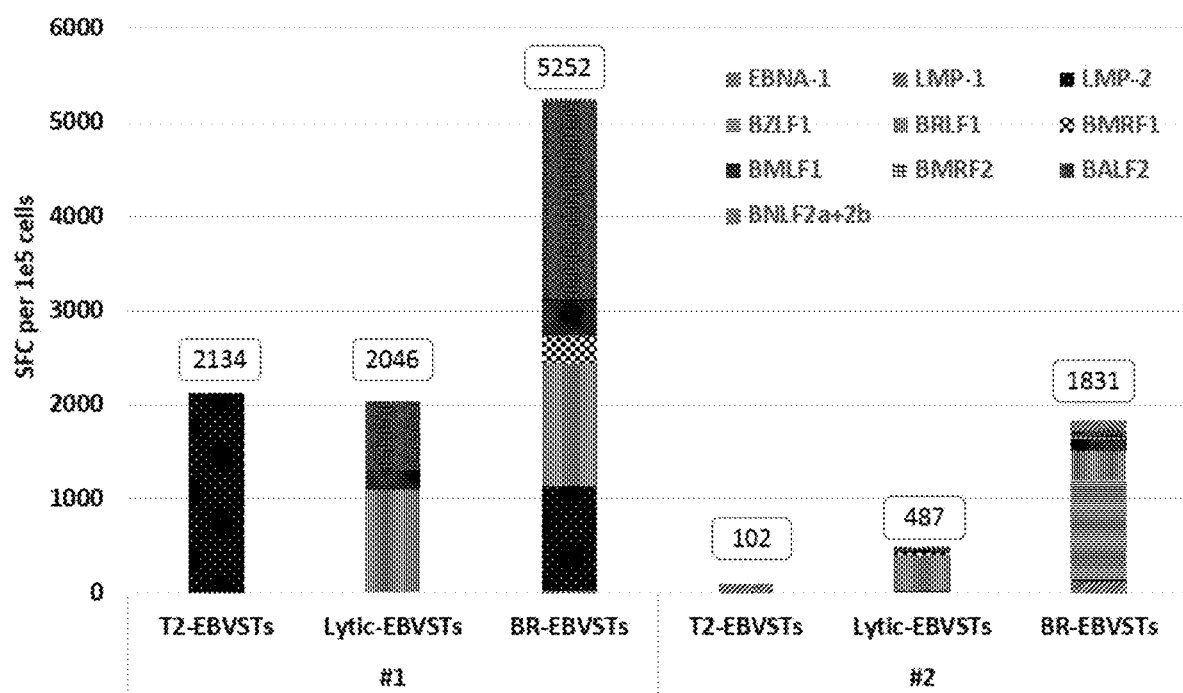
FIG. 2. Bar chart showing the number of spot-forming cells (SFCs) per 100,000 cells specific for the indicated EBV antigens, within EBVSTs expanded from PBMCs from two EBV-positive lymphoma patients by stimulation using latent pepmix (T2-EBVSTs), lytic pepmix (Lytic-EBVSTs) or latent+lytic pepmix (BR-EBVSTs). The total numbers of cells in bars is indicated.

FIG. 2 shows that the number of cells that secrete IFNγ in response to stimulation with pepmixes corresponding to EBV latent and lytic antigens is greater for EBVSTs generated using a combination of latent antigen and lytic antigen pepmixes, than for EBVSTs generated using latent antigen pepmixes alone, or lytic antigen pepmixes alone. There is a super-additive increase in the number of IFNγ-producing cells when a combination of latent antigen and lytic antigen pepmixes.

In further experiments, EBVSTs prepared from PBMCs of healthy donors using the different pepmixes were analysed by ELISPOT to determine their ability to recognise different EBV antigens, as described above.

Figure 3:
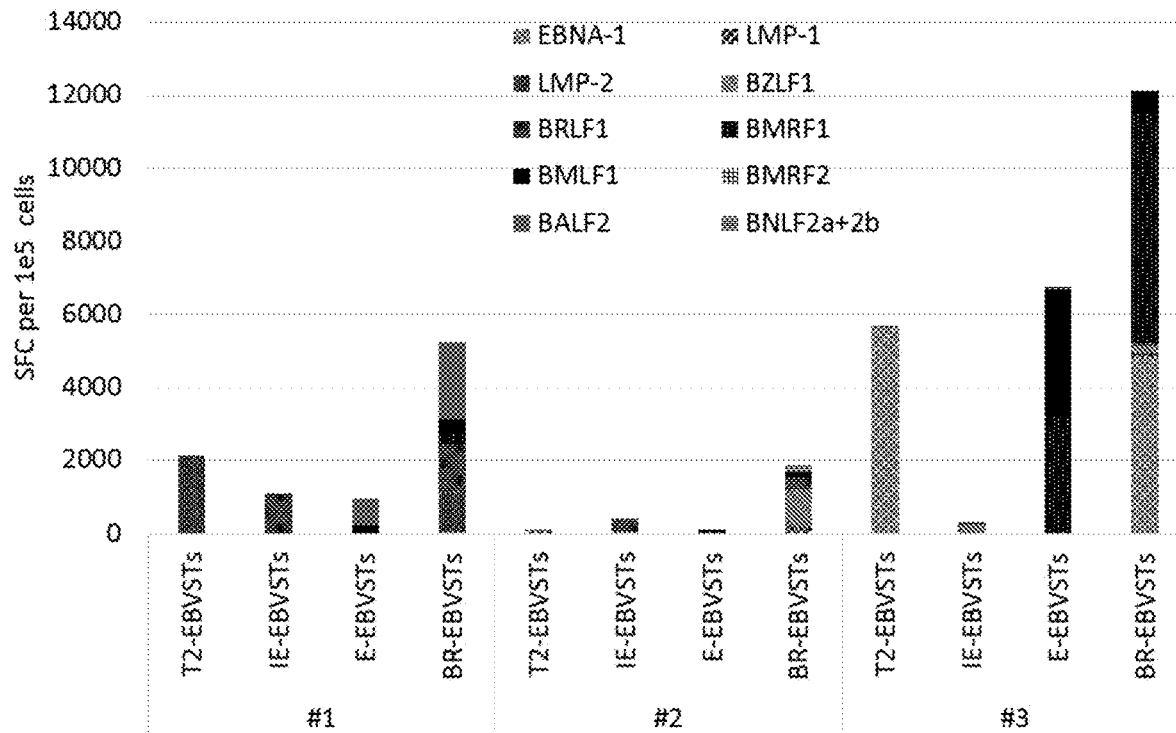
FIG. 3. Bar chart showing the number of spot-forming cells (SFCs) per 100,000 cells specific for the indicated EBV antigens, within EBVSTs expanded from PBMCs from three healthy donor subjects by stimulation using latent pepmix (T2-EBVSTs), immediate-early lytic pepmix (IE-EBVSTs), early lytic pepmix (E-EBVSTs), or latent+lytic pepmix (BR-EBVSTs).

The results are shown in FIG. 3, and demonstrate that it was possible to expand T cells specific for latent cycle antigens, immediate-early lytic antigens and early lytic antigens from PBMCs of healthy donors.

Example 3: Analysis of Cell Killing by EBVSTs Obtained by Stimulation of PBMCs with Pepmixes Corresponding to Different EBV Antigens EBVSTs obtained by stimulation of PBMCs using different pepmixes were analysed for their ability to kill autologous EBV-transformed B cell lines.

10 μl of $Cr^{51}$ was added to $1 \times 10^6$ autologous LCLs, which were pulsed with 10 ng EBV latent+lytic pepmixes (see (iii) of Example 1) and incubated at 37° C. for 1 hr. The LCLs were then washed 3 times with CTL media and resuspended in CTL media to 50,000 cells/ml. EBVSTs were plated with corresponding autologous, pepmix-pulsed LCLs at an Effector:Target cell ratio of 20:1 (100,000 EBVSTs+5,000 LCLs), in 200 μl CTL media in wells of a V-shaped well 96-well plates. The coculture was incubated at 37° C. at 5% $CO_2$ for 4 hrs. The supernatant was then harvested and % specific lysis of target cells was determined using a Gamma-ray counter to measure of $Cr^{51}$ released by killed target cells.

Figure 4:
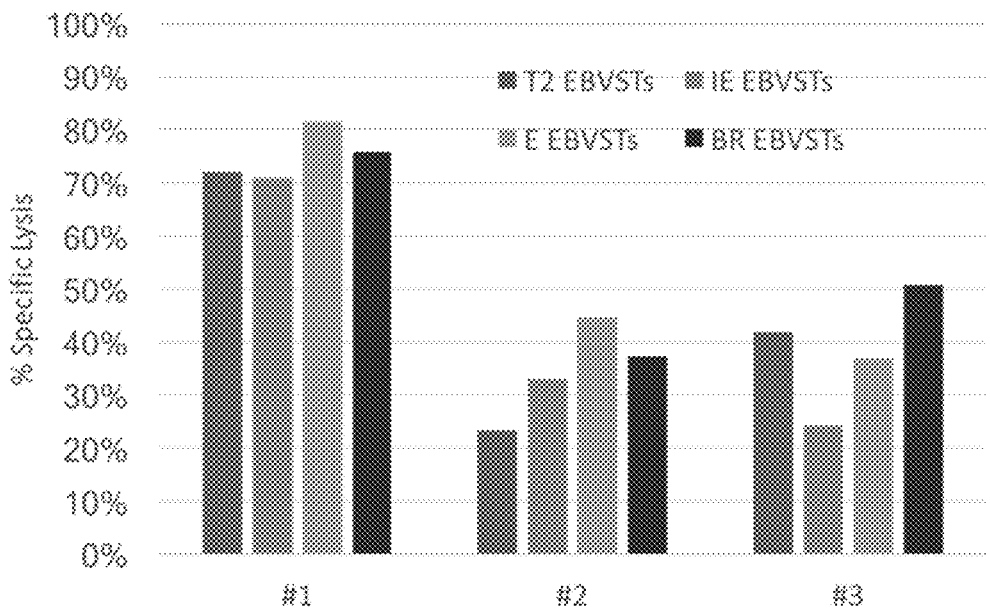
FIG. 4. Bar chart showing the percentage of autologous, EBV-LCLs lysed by EBVSTs expanded from PBMCs from three healthy donor subjects by stimulation using latent pepmix (T2-EBVSTs), immediate-early lytic pepmix (IE-EBVSTs), early lytic pepmix (E-EBVSTs), or latent+lytic pepmix (BR-EBVSTs), in an in vitro assay of cytolytic activity.

The results are shown in FIG. 4. EBV antigen-specific T-cells obtained by stimulation of PBMCs using different pepmixes were able to kill autologous EBV-transformed B-cell lines.

The potent ability of EBVSTs obtained using methods employing lytic antigen pepmixes to kill EBV-LCLs was surprising, because only a small proportion of the LCLs would be expected to be in the lytic cycle (and thus express the target antigen). The results may be explained by phagocytosis and presentation of antigens from dying cells in the lytic phase.

Example 4: Analysis of In Vivo Anti-Cancer Activity for EBVSTs Obtained by Stimulation of PBMCs with Pepmixes Corresponding to Different EBV Antigens The inventors investigated the comparative ability of BR-EBVSTs and T2-EBVSTs to treat EBV-positive cancer in vivo using a murine xenograft model.

Briefly, EBV-positive tumors were established by subcutaneous implantation of $3.5 \times 10^6$ firefly luciferase-expressing autologous LCLs in matrigel, into the flanks of NSG mice. 8 days later, when tumors were visible, mice were administered with PBS (control group), $5 \times 10^6$ BR-EBVSTs, or $5 \times 10^6$ T2-EBVSTs by intravenous injection.

Tumors were monitored throughout the experiment by bioluminescence imaging; luciferase activity was monitored by intraperitoneal injection of D-Luciferin (1.5 mg per mouse), and imaging of the mice 10 min later using an IVIS imager (Xenogen). Tumor volume was also monitored by measurement using calipers.

Figure 5:
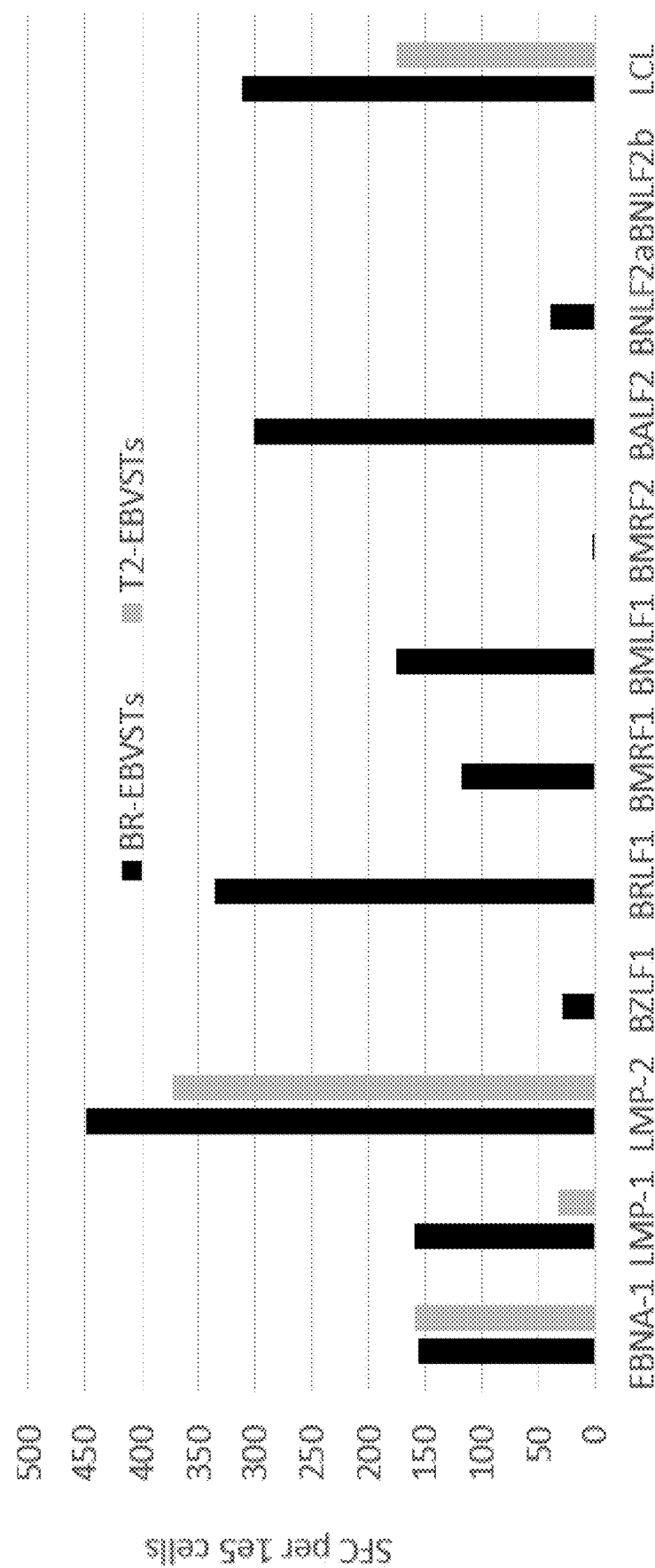
FIG. 5. Bar chart showing the number of spot-forming cells (SFCs) per 100,000 cells specific for the indicated EBV antigens or LCLs, within EBVSTs expanded from PBMCs by stimulation using latent pepmix (T2-EBVSTs), or latent+lytic pepmix (BR-EBVSTs).

Prior to infusion, the BR-EBVSTs and T2-EBVSTs were analysed by ELISPOT for their ability to produce IFNγ in response to stimulation with different EBV antigens or EBV-LCLs. The results are shown in FIG. 5, and demonstrate that populations of immune cells expanded using peptides corresponding to EBV latent and lytic antigens comprise cells reactive to both EBV latent and lytic antigens, and comprise a greater proportion of cells which produce IFNγ in response to stimulation with EBV-LCLs as compared to populations of immune cells expanded using peptides corresponding to EBV latent antigens only.

Figure 6A:
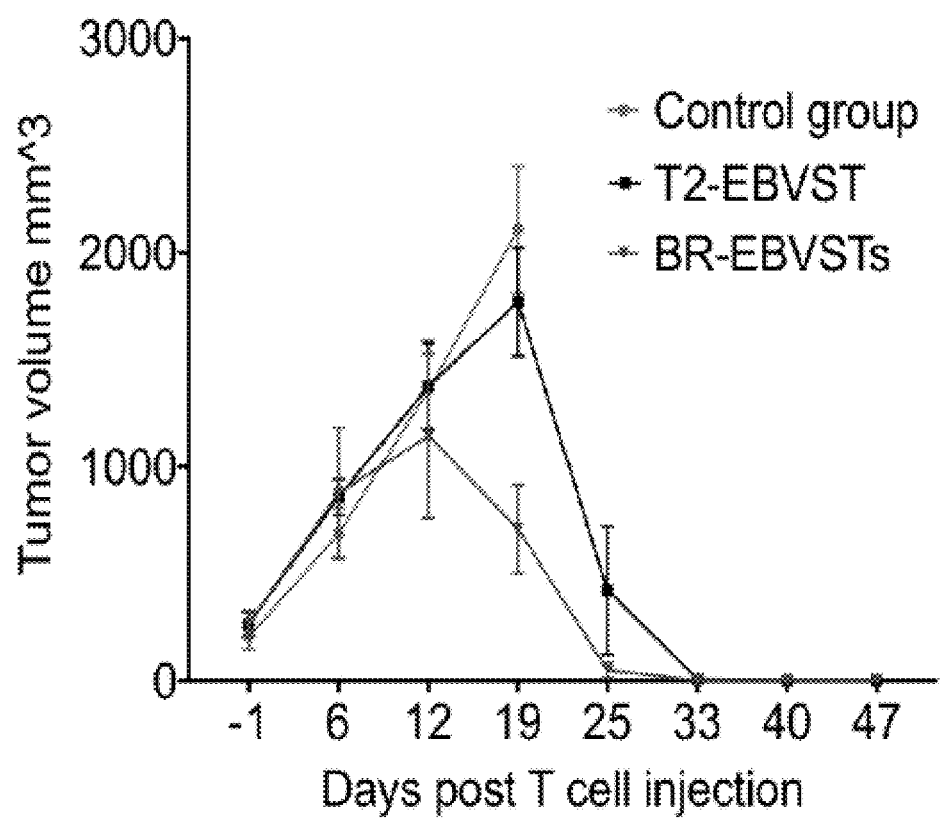
FIGS. 6A to 6C. Graphs and images showing the in vivo anti-cancer activity of EBVSTs expanded from PBMCs by stimulation using latent pepmix (T2-EBVSTs) or latent+lytic pepmix (BR-EBVSTs) against autologous EBV-LCLs, in a mouse xenograft model of EBV-positive cancer. A control group received PBS instead of EBVSTs.
Figure 6B:
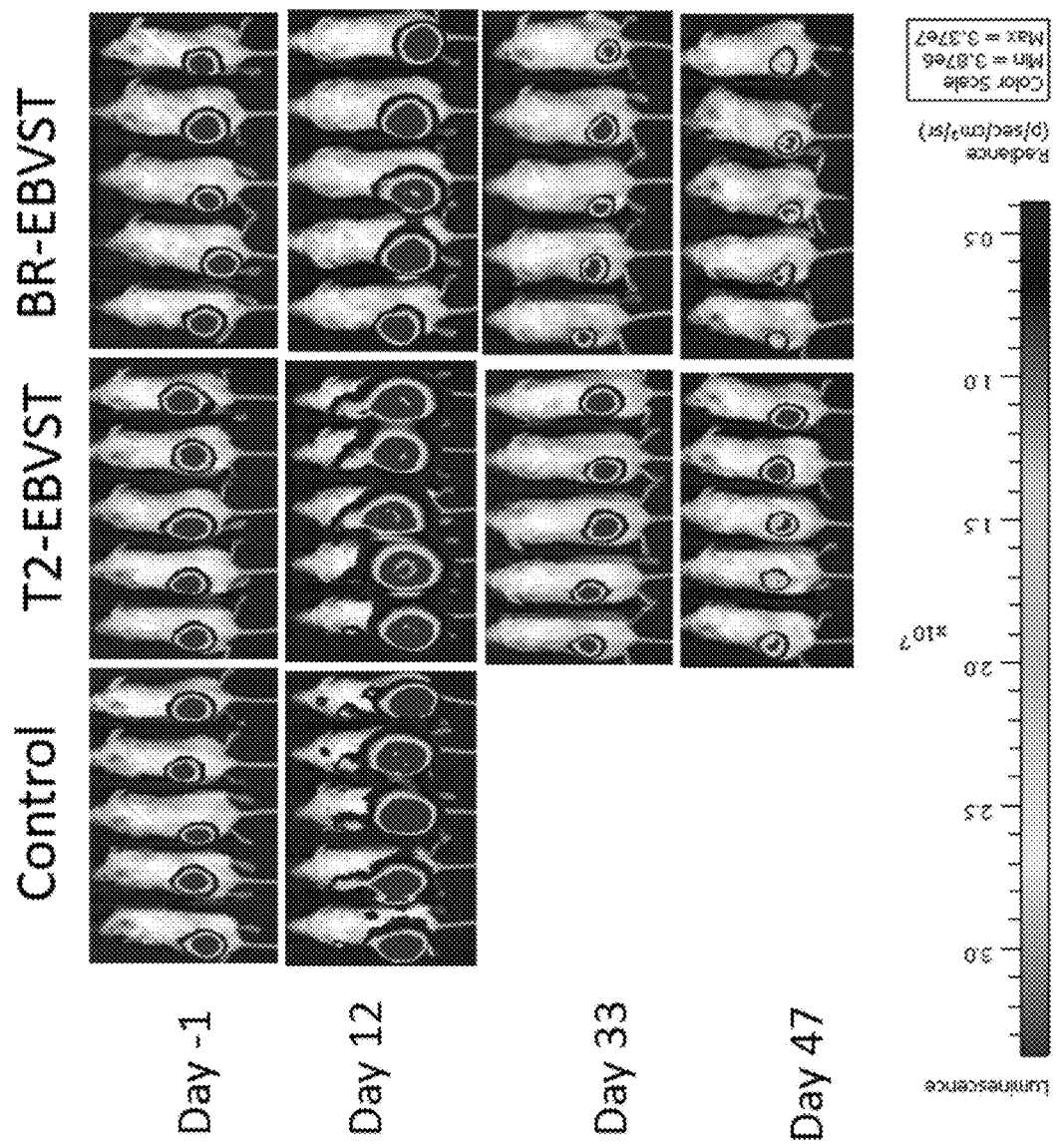
Figure 6C:
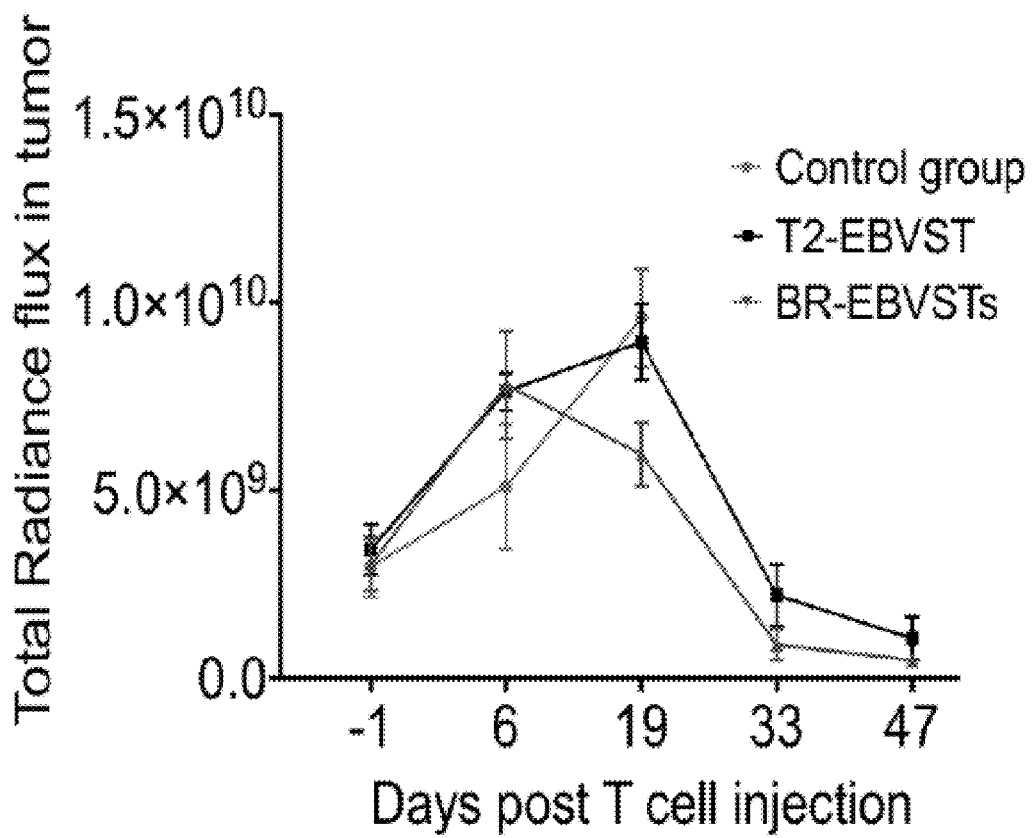
Figure 7:
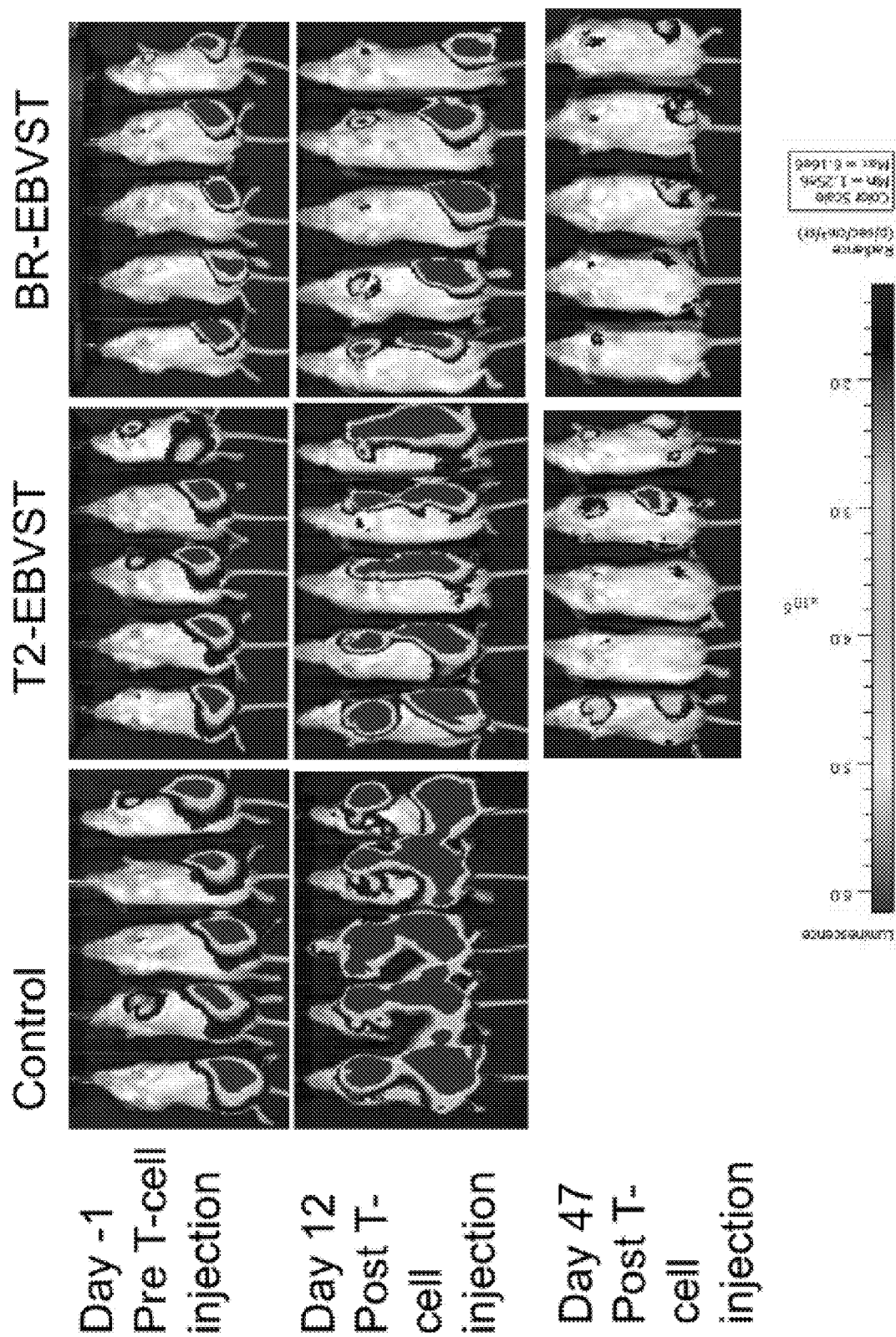
FIG. 7. Images showing the burden and location of firefly luciferase-expressing EBV-LCLs in vivo in mice at the indicated day of an experiment investigating the anti-cancer activity of EBVSTs expanded from PBMCs by stimulation using latent pepmix (T2-EBVSTs) or latent+lytic pepmix (BR-EBVSTs) against autologous EBV-LCLs, in a mouse xenograft model of EBV-positive cancer. A control group received PBS instead of EBVSTs.
Figure 8A:
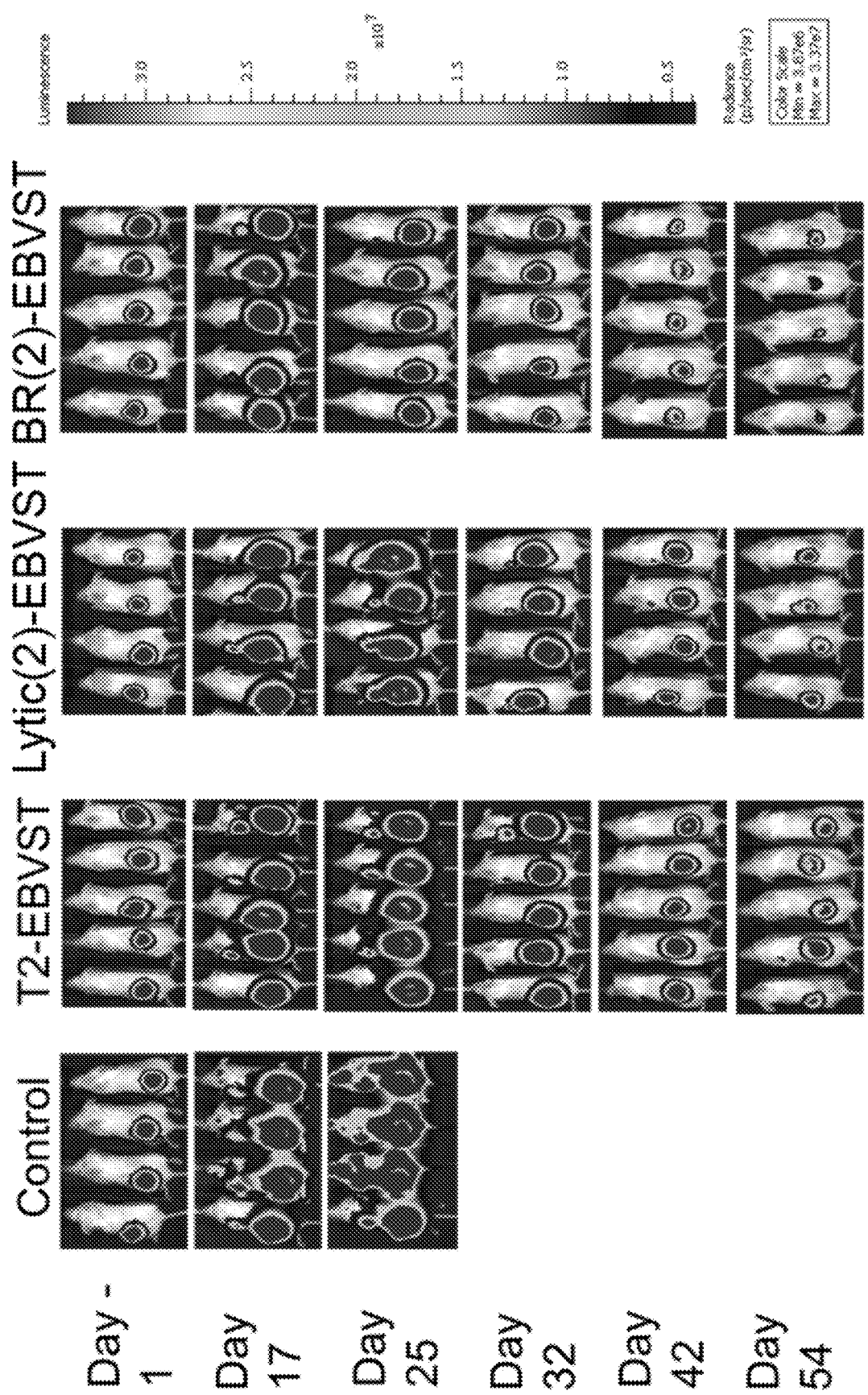
FIGS. 8A to 8D. Images and graphs showing the in vivo anti-cancer activity of EBVSTs expanded from PBMCs by stimulation using latent pepmix (T2-EBVSTs), lytic (2) pepmix (Lytic(2)-EBVSTs) or lytic (2)+latent pepmix (BR(2)-EBVSTs) against autologous EBV-LCLs, in a mouse xenograft model of EBV-positive cancer. A control group received PBS instead of EBVSTs.
Figure 8B:
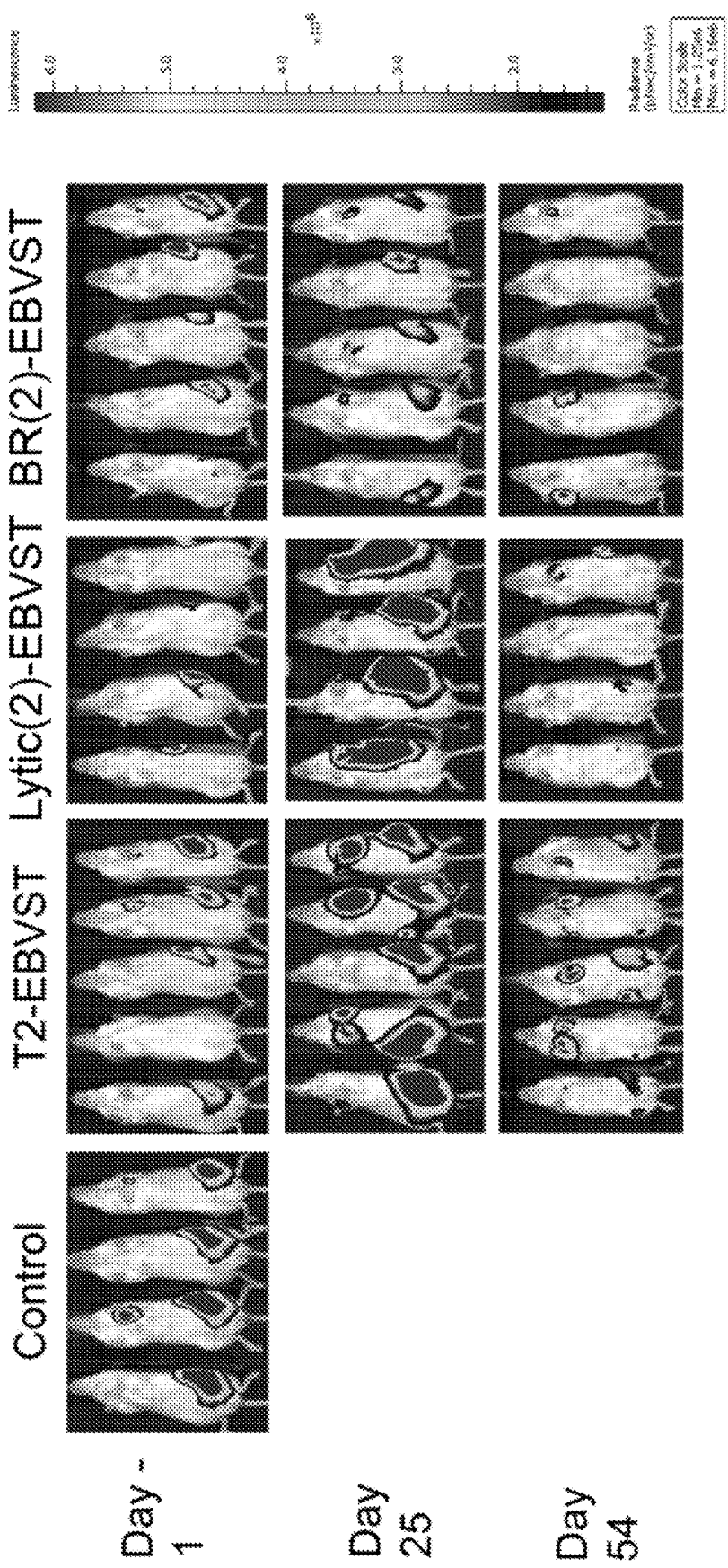
Figure 8C:
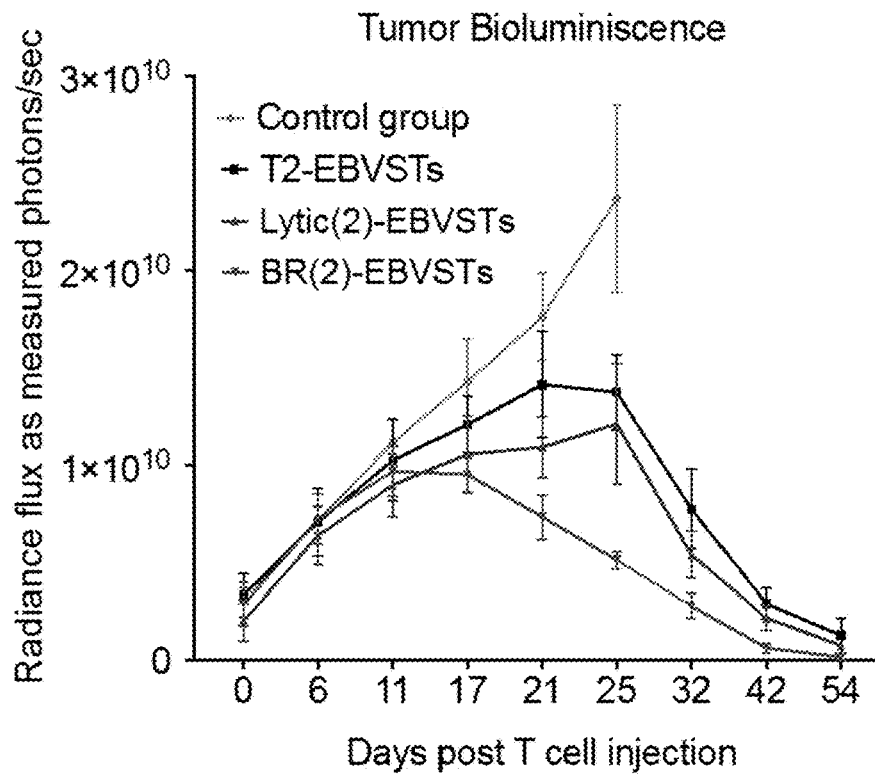
Figure 8D:
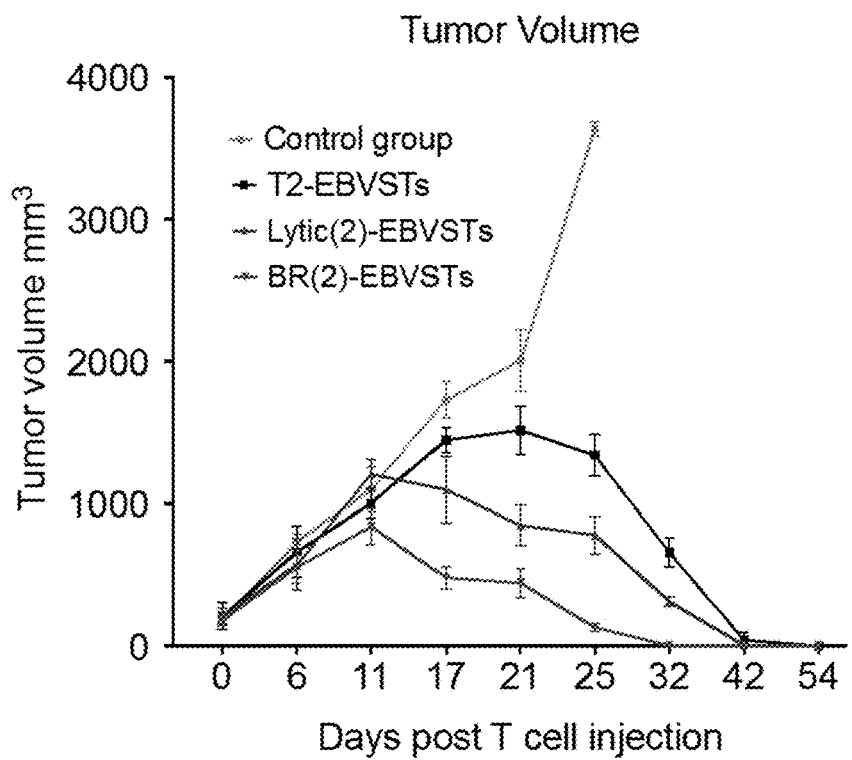

FIGS. 6 and 7 show that BR-EBVSTs more rapidly controlled EBV-positive tumors than T2-EBVSTs.

FIG. 7 also shows that BR-EBVST-treated mice displayed reduced metastasis than mice treated with T2-EBVSTs.

In a further experiment EBV-positive tumors were established by subcutaneous implantation of $3.5 \times 10^6$ firefly luciferase-expressing autologous LCLs as above, and 8 days later mice were administered with PBS (control group), $1 \times 10^6$ BR(2)-EBVSTs, $1 \times 10^6$ Lytic(2)-EBVSTs, or $1 \times 10^6$ T2-EBVSTs by intravenous injection.

The Lytic(2)-EVBSTs and BR(2)-EBVSTs used in this experiment were generated as described in Example 1, with the exception that the following combinations of pepmixes were used in stimulations to expand the EBVSTs:

(vi) BZLF1 pepmix+BRLF1 pepmix+BMRF1 pepmix+BMLF1 pepmix+BXLF1 pepmix+BALF1 pepmix+BLLF2 pepmix+BALF2 pepmix+BNLF2A pepmix—"Lytic (2) pepmixes"

(vii) EBNA1 pepmix+LMP1 pepmix+LMP2 pepmix+BZLF1 pepmix+BRLF1 pepmix+BMRF1 pepmix+BMLF1 pepmix+BXLF1 pepmix+BALF1 pepmix+BLLF2 pepmix+BALF2 pepmix+BNLF2A pepmix—"Lytic (2)+latent pepmixes"

Pepmixes for BMLF1, BXLF1, BALF1, BLLF2, BALF2 and BNLF2A were prepared by combining individual constituent peptides obtained from Genemed. The pepmixes for EBNA1, LMP1, LMP2, BZLF1, BRLF1 and BMRF1 were obtained from JPT technologies as shown in Example 1.

The EBVSTs generated by methods employing lytic pepmixes (i.e. (vi) above) are referred to as "Lytic(2)-EBVSTs", and the EBVSTs generated by methods employing lytic (2)+latent pepmixes (i.e. (vii) above) are referred to as "BR(2)-EBVSTs".

Tumors were monitored throughout the experiment by bioluminescence imaging as described above, and tumor volume was also monitored by measurement using calipers.

Blood plasma samples were also collected from the mice at days 3 and 8 post-EBVST administration, and analysed by ELISA in order to determine the levels of GM-CSF, IFNγ and IL-10.

The results are shown in FIGS. 8 and 9.

EBVSTs expanded by stimulations using peptides of EBV latent+lytic antigens strongly inhibited tumor growth (FIGS. 8A to 8D). EBVSTs expanded by stimulations using only EBV lytic antigens were also able to inhibit tumor growth, and did so to a similar or greater extent to EBVSTs expanded by stimulations using only EBV latent antigens.

Figure 9A:
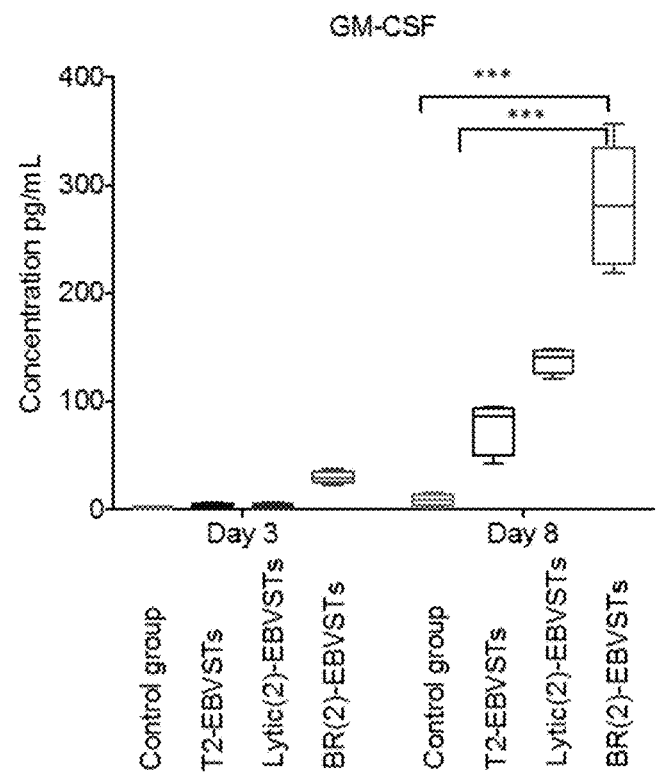
FIGS. 9A to 9C. Box plots showing the levels of cytokines detected in the serum of mice undergoing treatment with EBVSTs expanded from PBMCs by stimulation using latent pepmix (T2-EBVSTs), lytic (2) pepmix (Lytic(2)-EBVSTs) or lytic (2)+latent pepmix (BR(2)-EBVSTs), in a mouse xenograft model of EBV-positive cancer, at the indicated number of days post-EBVST injection.
Figure 9B:
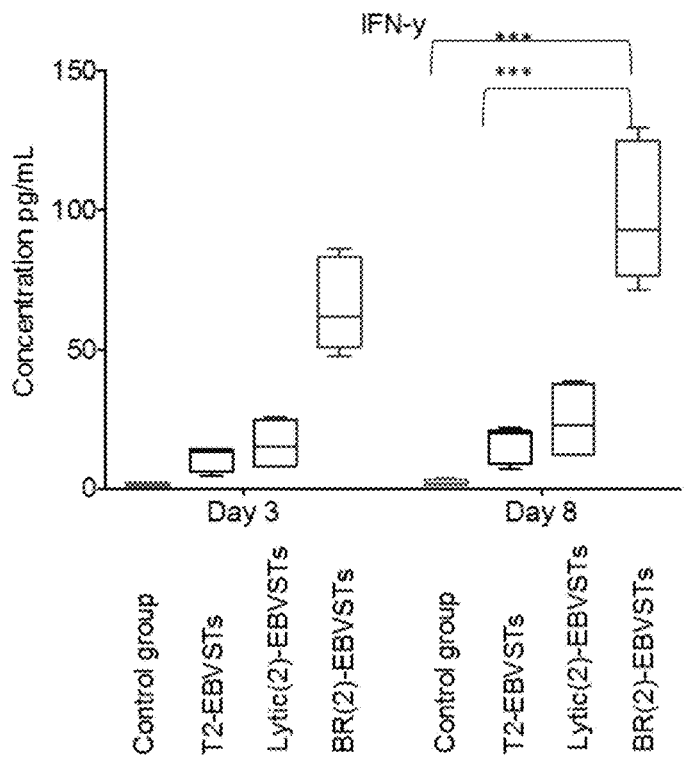

Mice treated with EBVSTs expanded by stimulations using peptides of EBV latent+lytic antigens also had increased levels of proinflammatory cytokines in their serum relative to mice treated with EBVSTs expanded by stimulations using only EBV latent antigens, whilst mice treated with EBVSTs expanded by stimulations using peptides of EBV lytic antigens only displayed similar or increased levels of proinflammatory cytokines in their serum relative to mice treated with EBVSTs expanded by stimulations using only EBV latent antigens (FIGS. 9A and 9B).

Figure 9C:
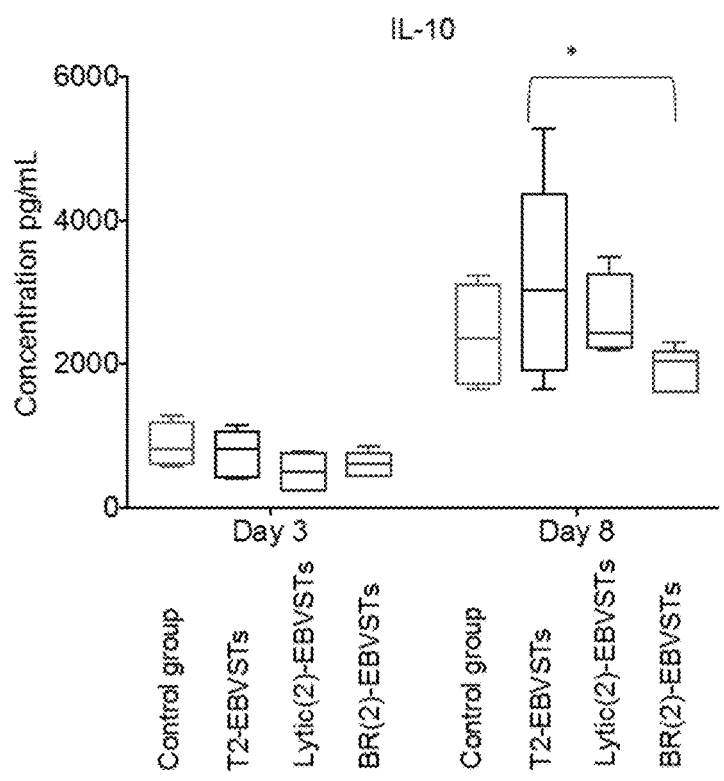

By contrast, Mice treated with EBVSTs expanded by stimulations using peptides of EBV latent+lytic antigens had reduced levels of IL-10 in their serum relative to mice treated with EBVSTs expanded by stimulations using only EBV latent antigens, whilst mice treated with EBVSTs expanded by stimulations using peptides of EBV lytic antigens only displayed similar or reduced levels of IL-10 in their serum relative to mice treated with EBVSTs expanded by stimulations using only EBV latent antigens (FIG. 9C).

So BR-EBVSTs were found to kill greater numbers of tumor cells and produce a greater amount of proinflammatory cytokines. Without wishing to be bound by any particular theory, this may result in a change in the tumor microenvironment leading to increased epitope spreading in vivo, and additional tumor cell killing by non-viral tumor antigen-specific T-cells.

Example 5: Conclusions

To summarise, the inventors have shown that:

Populations of T cells containing T cells specific for lytic and latent EBV antigens can be obtained by stimulating PBMCs from both healthy donors and lymphoma patients with pepmixes corresponding to lytic and latent EBV antigens (see e.g. FIGS. 1 and 3);

Stimulating PBMCs with pepmixes corresponding to lytic and latent EBV antigens yields more EBV antigen-reactive T cells than stimulations using pepmixes corresponding to lytic EBV antigens only, or latent EBV antigens only (see e.g. FIG. 2);

Populations of T cells obtained by stimulating PBMCs with pepmixes corresponding to lytic+latent EBV antigens, or immediate-early lytic antigens, or early lytic antigens are capable of killing EBV-LCLs, with similar ability as cells populations of T cells obtained by stimulating PBMCs with pepmixes corresponding latent EBV antigens (see e.g. FIG. 4);

Populations of T cells obtained by stimulating PBMCs with pepmixes corresponding to lytic+latent EBV antigens comprise a greater proportion of cells reactive for EBV-infected cells as compared to populations of T cells obtained by stimulating PBMCs with pepmixes corresponding latent EBV antigens only (see e.g. FIG. 5);

Populations of T cells obtained by stimulating PBMCs with pepmixes corresponding to lytic+latent EBV antigens display improved control of tumor growth and reduced metastasis for EBV-positive cancer as compared to populations of T cells obtained by stimulating PBMCs with pepmixes corresponding latent EBV antigens (see e.g. FIGS. 6 and 7).

Populations of T cells obtained by stimulating PBMCs with pepmixes corresponding lytic EBV antigens display similar or improved control of tumor growth for EBV-positive cancer as compared to populations of T cells obtained by stimulating PBMCs with pepmixes corresponding latent EBV antigens (see e.g. FIG. 8).

Subjects having EBV-positive cancer which are treated with T cells obtained by stimulating PBMCs with pepmixes corresponding to lytic+latent EBV antigens have elevated levels of proinflammatory cytokines (GM-CSF, IFNγ) and reduced levels of anti-inflammatory cytokines (IL-10) in the peripheral blood as compared to subjects treated with T cells obtained by stimulating PBMCs with pepmixes corresponding latent EBV antigens (see e.g. FIG. 9).

Subjects having EBV-positive cancer which are treated with T cells obtained by stimulating PBMCs with pepmixes corresponding to lytic EBV antigens have similar or elevated levels of proinflammatory cytokines (GM-CSF, IFNγ) and similar or reduced levels of anti-inflammatory cytokines (IL-10) in the peripheral blood as compared to subjects treated with T cells obtained by stimulating PBMCs with pepmixes corresponding latent EBV antigens (see e.g. FIG. 9).

Example 6: Generation of EBV-Specific T Cells from PBMCs Depleted of CD45RA-Positive Cells The inventors next investigated the effect of depleting PBMC populations of CD45RA-positive cells on the expanded population of EBV-specific T cells.

Outgrowth of NK cells from PBMC populations can be problematic in methods for expanding EBVSTs from NK cell populations due to IL-15-mediated stimulation of NK cell proliferation. CD45RA is a naïve T-cell marker that is also expressed on natural T-regulatory cells and NK cells, so it was reasoned that depletion of CD45RA+ cells would remove the NK cells from the starting PBMC population. Depletion of CD45RA+ cells also removes T regulatory cells that can inhibit the outgrowth of antigen-specific T-cells, especially in cancer patients, and also removes naïve cells that can grow as bystander cells and dilute the antigen-specific T-cells.

PBMCs were depleted of CD45RA-expressing cells using Miltenyi® columns and CD45RA-conjugated beads, and the PBMCs depleted of CD45RA-positive cells were subsequently used to expand EBV-specific T cells by stimulation with latent pepmixes essentially as described in Example 1.

PBMCs depleted of CD45RA-positive cells were also used as the starting population for producing ATCs used in restimulations, which were produced essentially as described in Example 1.

The following experimental conditions were compared:
(i) EBVSTs expanded from whole PBMCs (i.e. PBMCs not depleted of CD45RA-positive cells)+restimulations using ATCs produced from whole PBMCs—referred to in FIG. 10 as "WW" (i.e. whole+whole)
(ii) EBVSTs expanded from whole PBMCs+restimulations using ATCs produced from PBMCs depleted of CD45RA-positive cells—referred to in FIG. 10 as "WD" (i.e. whole+depleted)
(iii) EBVSTs expanded from PBMCs depleted of CD45RA-positive cells+restimulations using ATCs produced from whole PBMCs—referred to in FIG. 10 as "DW" (i.e. depleted+whole)
(iv) EBVSTs expanded from PBMCs depleted of CD45RA-positive cells+restimulations using ATCs produced from PBMCs depleted of CD45RA-positive cells—referred to in FIG. 10 as "DD" (i.e. depleted+depleted)

EBVSTs prepared according to (i) to (iv) above from PBMCs obtained from four different healthy donors (D #1 to D #4) were analysed by ELISPOT to determine their ability to recognise different EBV antigens. ELISPOT analysis was performed essentially as described in Example 2.

Figure 10:
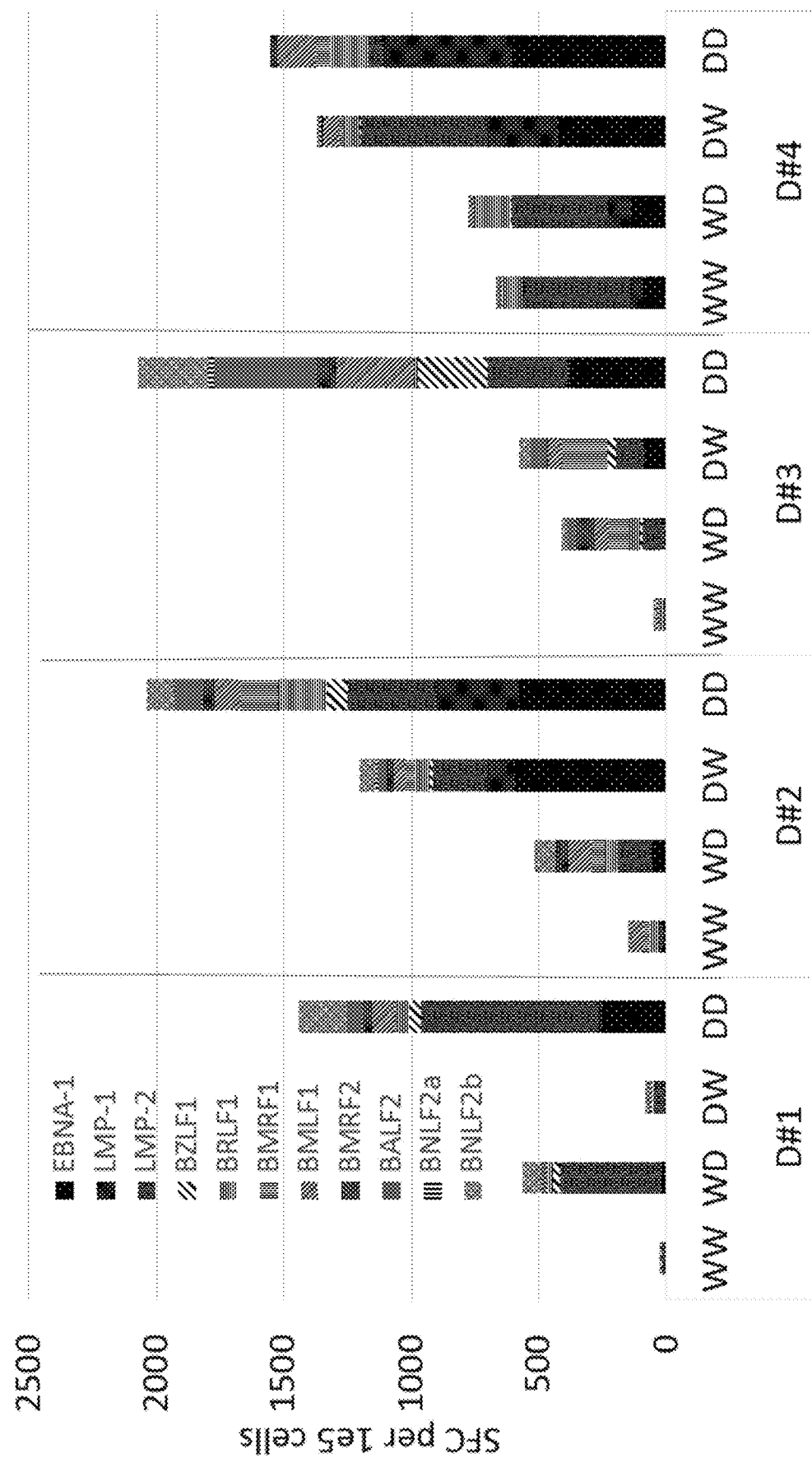
FIG. 10. Bar chart showing the number of spot-forming cells (SFCs) per 100,000 cells specific for EBV antigens, within populations of cells expanded by stimulation using latent pepmix from PBMCs obtained from four different healthy donor subjects (D #1 to D #4). WW=EBVSTs expanded from whole PBMCs, and restimulated using ATCs derived from whole PBMCs; WD=EBVSTs expanded from whole PBMCs, and restimulated using ATCs derived from PBMCs depleted of CD45RA-positive cells; DW=EBVSTs expanded from PBMCs depleted of CD45RA-positive cells, and restimulated using ATCs derived from whole PBMCs; and DD=EBVSTs expanded from PBMCs depleted of CD45RA-positive cells, and restimulated using ATCs derived from PBMCs depleted of CD45RA-positive cells FIG. 11. Histograms showing expression of CD80 and HLA-DR on ATCs derived from four different healthy donor subjects (D #1 to D #4), from whole PBMCs, or from PBMCs depleted of CD45RA-positive cells, as determined by flow cytometry.

The results are shown in FIG. 10. For each donor, using PBMCs depleted of CD45RA-positive cells as the starting population for expanding EBVSTs yielded an increased proportion of cells in the expanded population that secrete IFNγ in response to stimulation with EBV pepmixes, as compared to methods using whole PBMC populations. Similarly, using PBMCs depleted of CD45RA-positive cells as the starting population for generating ATCs used in restimulations resulted in a greater proportion of cells in the expanded population that secrete IFNγ in response to stimulation with EBV pepmixes.

The inventors analysed expression of the costimulatory molecule CD80 and HLA-DR (MHC class II) on the ATCs generated from whole PBMCs, or from PBMCs depleted of CD45RA-positive cells, by flow cytometry.

Figure 11:
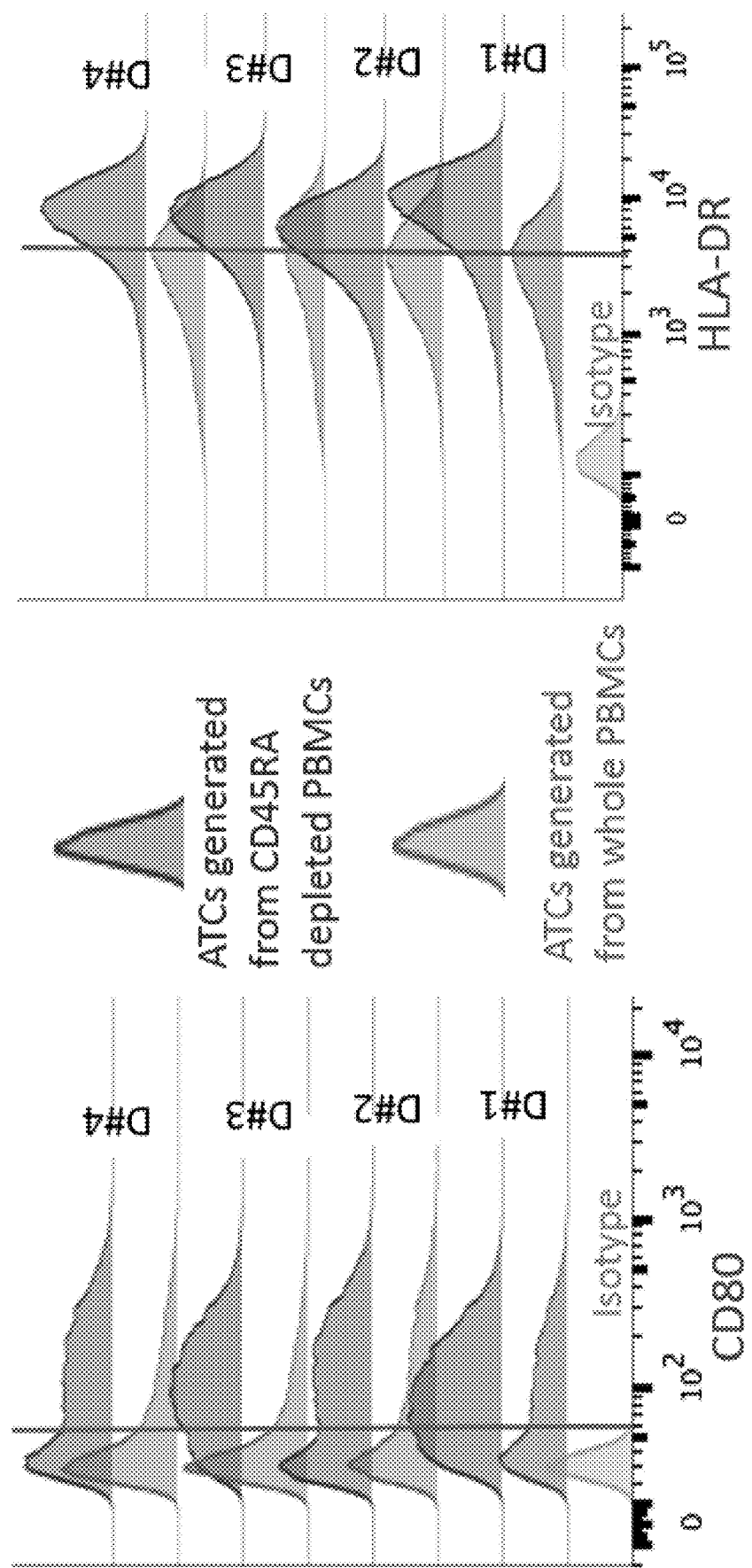

The results are shown in FIG. 11. The ATCs generated from PBMCs depleted of CD45RA-positive cells had higher expression of CD80 and HLA-DR, and thus improved antigen-presenting and costimulatory properties as compared to ATCs generated from whole PBMCs.

The invention claimed is:

1. A method of producing a population of immune cells comprising immune cells specific for an Epstein Barr Virus (EBV) lytic antigen, comprising:
(a) stimulating immune cells specific for an EBV lytic antigen by contacting peripheral blood mononuclear cells (PBMCs) with:
(i) one or more peptides corresponding to all or part of one or more EBV lytic antigens; or
(ii) antigen presenting cells (APCs) which have been cultured in vitro in the presence of one or more peptides corresponding to all or part of one or more EBV lytic antigens, and which therefore present the one or more peptides,
wherein the one or more EBV lytic antigens comprise an EBV lytic antigen selected from BRLF1, BMLF1, BMRF1, BXLF1, BALF1, BALF2, BGLF5, BHRF1, BNLF2A, BNLF2B, BHLF1, BLLF2, BKRF4, BMRF2, BALF4, BILF1, BILF2, BNFR1, BVRF2, BALF3, BALF5 and BDLF3; and
(b) formulating the population of immune cells obtained at step (a) to a pharmaceutical composition suitable for administration to a human subject.

2. The method according to claim 1, wherein step (a) further comprises re-stimulating the immune cells specific for an EBV lytic antigen by contacting them with APCs presenting one or more peptides corresponding to all or part of one or more EBV lytic antigens.

3. The method according to claim 1, wherein the one or more EBV lytic antigens comprise an EBV lytic antigen selected from BRLF1, BMLF1, BMRF1, BALF2, BNLF2A, BNLF2B, BMRF2 and BDLF3.

4. The method according to claim 1, wherein the PBMCs are PBMCs depleted of CD45RA-positive cells.

5. A method of producing a population of immune cells comprising immune cells specific for an Epstein Barr Virus (EBV) lytic antigen and immune cells specific for an EBV latent antigen, comprising:
(a) stimulating immune cells specific for an EBV lytic antigen and immune cells specific for an EBV latent antigen by contacting peripheral blood mononuclear cells (PBMCs) with:
(i) one or more peptides corresponding to all or part of one or more EBV lytic antigens, and one or more peptides corresponding to all or part of one or more EBV latent antigens; or
(ii) antigen presenting cells (APCs) which have been cultured in vitro in the presence of one or more peptides corresponding to all or part of one or more EBV lytic antigens, and one or more peptides corresponding to all or part of one or more EBV latent antigens, and which therefore present the one or more peptides,
wherein the one or more EBV lytic antigens comprise an EBV lytic antigen selected from BRLF1, BMLF1, BMRF1, BXLF1, BALF1, BALF2, BGLF5, BHRF1, BNLF2A, BNLF2B, BHLF1, BLLF2, BKRF4, BMRF2, BALF4, BILF1, BILF2, BNFR1, BVRF2, BALF3, BALF5 and BDLF3; and
(b) formulating the population of immune cells obtained at step (a) to a pharmaceutical composition suitable for administration to a human subject.

6. The method according to claim 5, wherein step (a) further comprises re-stimulating the immune cells specific for an EBV lytic antigen and the immune cells specific for an EBV latent antigen by contacting them with APCs presenting one or more peptides corresponding to all or part of one or more EBV lytic antigens, and one or more peptides corresponding to all or part of an EBV latent antigen.

7. The method according to claim 5, wherein the one or more EBV lytic antigens comprise an EBV lytic antigen selected from BRLF1, BMLF1, BMRF1, BALF2, BNLF2A, BNLF2B, BMRF2 and BDLF3.

8. The method according to claim 5, wherein the one or more EBV latent antigens are selected from EBNA1, EBNA-LP, EBNA2, EBNA3A, EBNA3B, EBNA3C, BARF1, LMP1, LMP2A and LMP2B.

9. The method according to claim 5, wherein the one or more EBV latent antigens are selected from EBNA1, LMP1, LMP2A and LMP2B.

10. The method according to claim 5, wherein the PBMCs are PBMCs depleted of CD45RA-positive cells.

11. An isolated population of immune cells obtained or obtainable by a method according to claim 1.

12. A method for treating or preventing an EBV-associated cancer, comprising administering an isolated population of immune cells according to claim 11 to a subject.

13. The method according to claim 12, wherein the EBV-associated cancer is selected from EBV-positive lymphoma, EBV-positive nasopharyngeal carcinoma, and EBV-positive gastric carcinoma.

* * * * *